(12) United States Patent
Van Wyk et al.

(10) Patent No.: US 7,566,333 B2
(45) Date of Patent: *Jul. 28, 2009

(54) ELECTROSURGICAL DEVICE WITH FLOATING-POTENTIAL ELECTRODE AND METHODS OF USING THE SAME

(75) Inventors: Robert A. Van Wyk, Largo, FL (US); Yuval Carmel, Rockville, MD (US); Anatoly Shkvarunets, Rockville, MD (US)

(73) Assignee: Electromedical Associates LLC, Bethesda, MD (US)

( * ) Notice: Subject to any disclaimer, the term of this patent is extended or adjusted under 35 U.S.C. 154(b) by 570 days.

This patent is subject to a terminal disclaimer.

(21) Appl. No.: 11/136,514

(22) Filed: May 25, 2005

(65) Prior Publication Data
US 2005/0234446 A1    Oct. 20, 2005

Related U.S. Application Data

(63) Continuation-in-part of application No. 10/911,309, filed on Aug. 4, 2004.

(60) Provisional application No. 60/648,105, filed on Jan. 28, 2005, provisional application No. 60/493,729, filed on Aug. 11, 2003.

(51) Int. Cl.
*A61B 18/18* (2006.01)

(52) U.S. Cl. .......................................... 606/41; 606/49

(58) Field of Classification Search ................. 606/41, 606/45, 49, 1, 32, 50, 46, 48, 40, 39, 42; 604/114, 22; 607/99, 101
See application file for complete search history.

(56) References Cited

U.S. PATENT DOCUMENTS

| | | | | |
|---|---|---|---|---|
| 5,647,840 A * | 7/1997 | D'Amelio et al. | ........... | 600/169 |
| 5,697,536 A * | 12/1997 | Eggers et al. | ............... | 604/114 |
| 5,709,698 A * | 1/1998 | Adams et al. | ............... | 606/180 |
| 6,169,926 B1 * | 1/2001 | Baker | ......................... | 607/99 |
| 6,235,020 B1 * | 5/2001 | Cheng et al. | .................. | 606/34 |
| 6,379,351 B1 * | 4/2002 | Thapliyal et al. | .............. | 606/41 |
| 6,468,274 B1 * | 10/2002 | Alleyne et al. | ................ | 606/41 |
| 6,582,423 B1 * | 6/2003 | Thapliyal et al. | .............. | 606/32 |
| 6,770,070 B1 * | 8/2004 | Balbierz | ...................... | 606/41 |
| 6,920,883 B2 * | 7/2005 | Bessette et al. | ............. | 128/898 |
| 2001/0001314 A1 * | 5/2001 | Davison et al. | ............... | 606/41 |
| 2002/0120261 A1 * | 8/2002 | Morris et al. | ................. | 606/41 |
| 2002/0133148 A1 * | 9/2002 | Daniel et al. | .................. | 606/34 |
| 2002/0133149 A1 * | 9/2002 | Bessette | ...................... | 606/41 |
| 2004/0006336 A1 * | 1/2004 | Swanson | ...................... | 606/41 |
| 2004/0006339 A1 * | 1/2004 | Underwood et al. | .......... | 606/45 |
| 2004/0104455 A1 * | 6/2004 | Shimizu | ...................... | 257/659 |

* cited by examiner

*Primary Examiner*—Michael Peffley
(74) *Attorney, Agent, or Firm*—Chalin A. Smith; Smith Patent Consulting

(57) ABSTRACT

The present invention relates to electrosurgical probes suitable for tissue vaporization and cutting of tissue structures, more particularly for performing electrosurgical cutting, ablation (volumetric tissue vaporization), coagulating and/or modification within a body tissue, cavity or vessel or on the surface of a patient. The system and method of the present invention optionally include structure for irrigation and/or aspiration of the surgical site and therefore may be used in relatively dry environments such as in the context of oral, otolaryngological, laparoscopic, and dermatologic procedures.

22 Claims, 27 Drawing Sheets

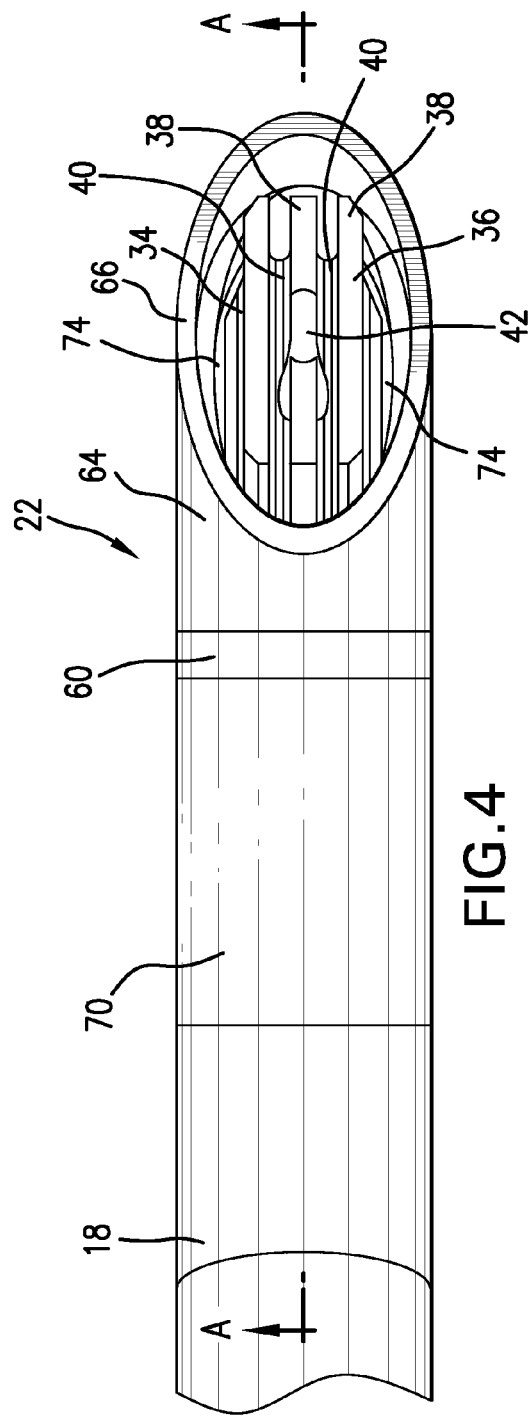
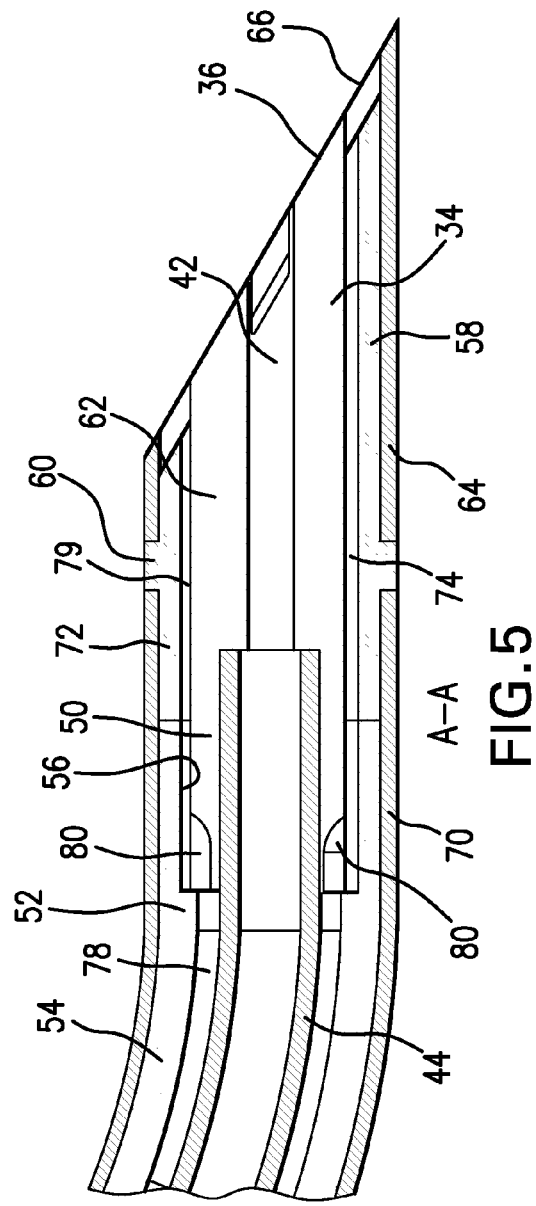

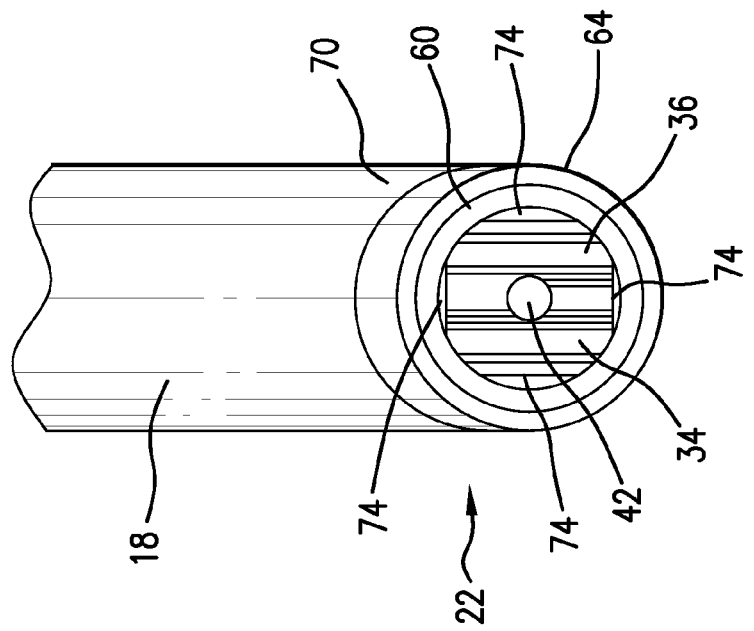
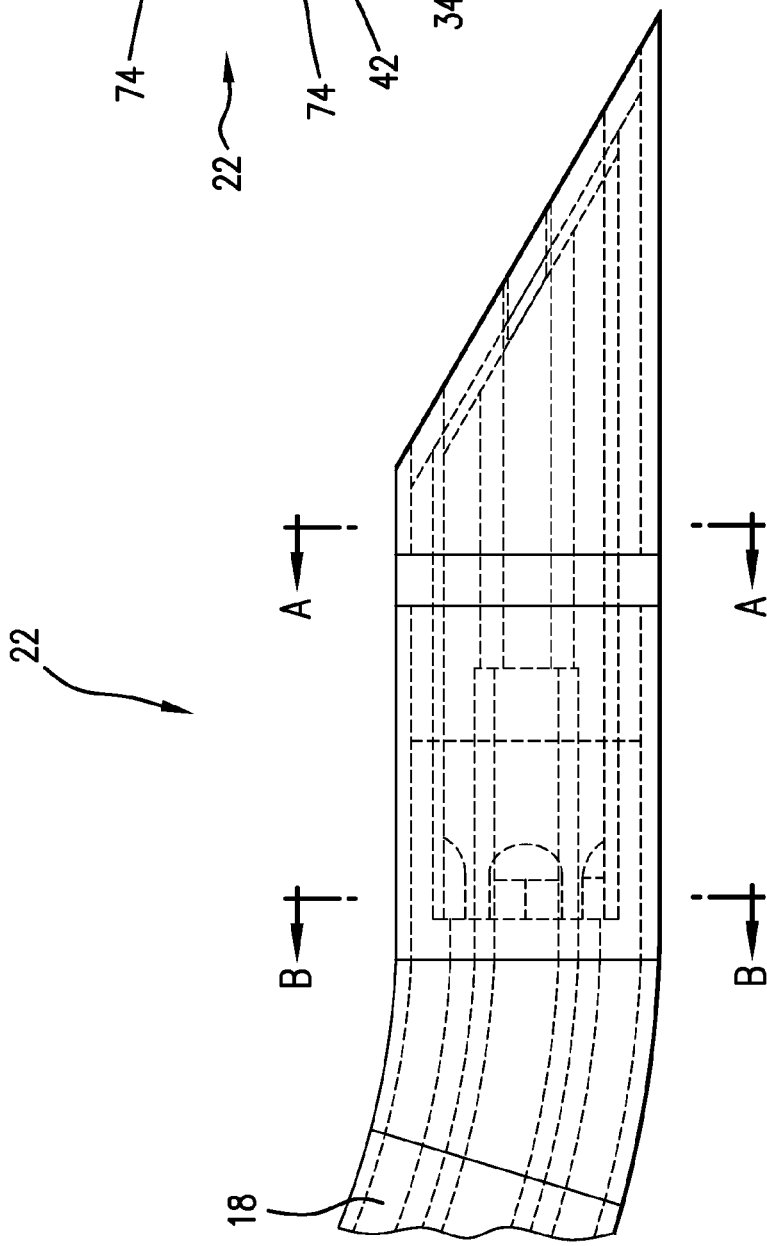

A-A

B-B

ELECTROSURGICAL DEVICE WITH FLOATING-POTENTIAL ELECTRODE AND METHODS OF USING THE SAME

PRIORITY

This application claims the benefit of U.S. Provisional Application Ser. No. 60/648,105 filed Jan. 28, 2005. In addition, this application is a continuation-in-part of co-pending U.S. patent application Ser. No. 10/911,309 filed Aug. 4, 2004 which, in turn, claims the benefit of U.S. Provisional Application Ser. No. 60/493,729 filed Aug. 11, 2003. The contents of these three applications are hereby incorporated by reference herein in their entirety.

FIELD OF THE INVENTION

The present invention relates generally to the field of electrosurgery, and, more particularly, to high efficiency surgical devices and methods which use of high frequency (RF) electrical power for cutting, bulk removal by vaporization (ablation), coagulation and treatment of tissue in a conductive liquid environment, as well as other forms of tissue treatment such as shrinking, lesion formation, sculpting and thermal treatment with or without externally supplied liquids.

BACKGROUND OF THE INVENTION

The present invention provides a system and method for performing electrosurgical cutting, ablation (volumetric tissue vaporization), coagulating or modification within a body tissue, cavity or vessel on the surface of a patient. The system and method of the invention herein disclosed may be used in relatively dry environments for, for instance, oral, otolaryngological, laparoscopic, and dermatologic procedures.

Electrosurgical procedures require a proper electrosurgical generator, which supplies the Radio Frequency (RF) electrical power, and a proper surgical electrode (also known as an electrosurgical probe). Under appropriate conditions the desired surgical effects are accomplished.

Note: in common terminology and as used herein the term "electrode" may refer to one or more components of an electrosurgical device (such as an active electrode or a return electrode) or to the entire device, as in an "ablator electrode". Electrosurgical devices may also be referred to as "probes".

Electrosurgical procedures rely on the application of RF electrical power using an electrode (or probe) for cutting, ablation or coagulation of tissue structures in a joint space which is filled by liquid. Many types of electrosurgical devices can be used; however, they can be divided to two general categories: monopolar devices and bipolar devices. When monopolar electrosurgical devices are used, the RF current generally flows from an exposed active electrode, through the patient's body, to a passive, return current electrode that is externally attached to a suitable location on the patient body. In this way the patient's body is part of the return current circuit. When bipolar electrosurgical devices are used, both the active and the return current electrodes are exposed, and are typically positioned in close proximity to each other and the active site. The RF current flows from the active electrode to the return electrode, through the nearby tissue and conductive fluids. Monopolar and bipolar devices in many fields of electrosurgery operate according to the same principles.

During the last several years, specialized arthroscopic electrosurgical probes called ablators have been developed. Examples of such instruments include ArthroWands manufactured by Arthrocare (Sunnyvale, Calif.), VAPR electrodes manufactured by Mitek Products Division of Johnson & Johnson (Westwood, Mass.) and electrodes by Stryker Corporation (Kalamazoo, Mich.) and Smith and Nephew Endoscopy (Andover, Mass.). These ablators differ from conventional electrosurgical probes in that they are designed for the bulk removal of tissue by vaporization in a conductive liquid environment, rather than for the cutting of tissue or for coagulation of bleeding vessels.

Recently the use of electrosurgery with conductive fluids for urology, gynecology and other procedures is also becoming popular. Previously, mostly non-conductive fluids were used for these applications.

While standard electrodes are capable of ablation (bulk vaporization), their geometries are not efficient for accomplishing this task. During ablation, water within the target tissue is vaporized. Because volumes of tissue are vaporized rather than discretely cut out and removed from the surgical site, the power requirements of ablator electrodes are generally higher than those of other arthroscopic electrosurgical electrodes. The geometry and design of the electrode and the characteristics of the RF power supplied to the electrode greatly affect the power required for ablation (vaporization) of tissue. Electrodes with inefficient designs require higher power levels than those with efficient designs.

During electrosurgery procedures in conductive fluids, most of the RF energy delivered to an electrode is dissipated in the fluid and in the adjacent tissue as heat, thereby raising the temperature of the fluid within the cavity and of the adjacent tissue. A substantial fraction of the RF power is used for the creation of sparks (arcs) in the vicinity of the electrodes. These sparks accomplish the tissue vaporization and cutting. In summary, the sparks are essential for tissue vaporization (ablation), while heating of the liquid and tissue away from the active electrode tip always occurs but has no desirable clinical effect.

The heating of the irrigation fluid and especially the adjacent tissue is not beneficial to the patient. On the contrary, this may substantially increase the likelihood of patient burns. For this and other reasons, improved, efficient electrosurgical electrodes are desirable for tissue vaporization and cutting of tissue structures.

An electrosurgical probe, in general, is composed of a metallic conductor surrounded by a dielectric insulator (e.g., formed of plastic, ceramic or glass) along the length, with the exception of the exposed metallic electrode. The probe electrode is often immersed in a conducting fluid, either filling a natural or created cavity or applied as irrigant to a "dry" site, and is brought in contact with the tissue structure during the electrosurgical procedure. The probe is energized, typically at a voltage of few hundred to a few thousand volts, using an RF generator operating at a frequency between 100 kHz to over 4 MHz. This voltage induces a current in the conductive liquid and nearby tissue. This current heats the liquid and tissue, the most intense heating occurring in the region very close to the electrode where the current density is highest. At points where the current density is sufficiently high, the liquid boils locally and many steam bubbles are created, the steam bubbles eventually insulating part or all of the electrode. Electrical breakdown in the form of an arc (spark) occurs in the bubbles which insulate the electrode. The sparks in these bubbles are channels of high temperature ionized gas, or plasma (temperature of about a few thousand degrees Kelvin). These high current density sparks, heat, evaporate (ablate) or cut the tissue (depending on the specific surgical procedure and the probe geometry) that is in contact with the spark.

The spark generation and tissue heating, modification or destruction very close to the electrode tip are a beneficial and desirable effect. At the same time, the induced current heats liquid and tissue farther away from the immediate vicinity of the electrode tip. This heating is undesirable and potentially dangerous because it may uncontrollably damage tissue structures in surrounding areas and also deep under the surface. The design of higher efficiency probes is desirable as it would lead to less heating of fluid and tissue not in close proximity, and give the surgeon a larger margin of safety during the procedure.

Ablation (vaporizing) electrodes currently in use, whether monopolar or bipolar, have an active electrode surrounded by an insulator significantly larger in size than the ablating surface of the electrode. For ablators with a circular geometry, the diameter of the portion of the probe which generates ablative arcs (the "working" diameter) is generally not greater than 70 to 80 percent of the diameter of the insulator (the "physical" diameter) and therefore only about 50% of the physical probe area can be considered effective. This increases the size of the distal end of the electrode necessary to achieve a given ablative surface size, and, for some procedures performed in internal body cavities, necessitates the use of large bore cannulae, an undesirable condition.

Many surgical procedures are not performed inside a natural or formed body cavity and as such are not performed on structures submerged under a conductive liquid. In laparoscopic procedures, for instance, the abdominal cavity is pressurized with carbon dioxide to provide working space for the instruments and to improve the surgeon's visibility of the surgical site. Other procedures, such as oral surgery, the ablation and necrosis of diseased tissue, or the ablation of epidermal tissue, are also typically performed in an environment in which the target tissue is not submerged. In such cases, it is necessary to provide a conductive irrigant to the region surrounding the active electrode(s), and frequently also to aspirate debris and liquid from the site. Such irrigant may be applied by a means external to the instrument; however, having an irrigation means internal or attached to the instrument generally provides better control and placement. This is also true for aspiration of fluid and debris. External means may be used for aspiration from the site; however, aspiration through the instrument distal end provides improved fluid control and may, in some cases, draw tissue toward the active electrode thereby enhancing performance.

Electrosurgical devices having means for irrigating a site, and/or means for aspirating fluid, bubbles and debris from a site are well known. Smith, in U.S. Pat. No. 5,195,959, disclose an electrosurgical device with suction and irrigation. Bales, et al., in U.S. Pat. No. 4,682,596 disclose a catheter for electrosurgical removal of plaque buildup in blood vessels, the catheter having lumens for supplying irrigant to the region of the instrument distal tip and for aspirating debris from the region. Hagen, in U.S. Pat. No. 5,277,696, discloses a high frequency coagulation instrument with means for irrigation and aspiration from the region of the instrument tip. Pao, in U.S. Pat. No. 6,674,499, discloses a coaxial bipolar probe with suction and/or irrigation. Eggers, in U.S. Pat. No. 6,066,134, discloses a method for electrosurgical cutting and coagulation which uses a bipolar probe having means for irrigating and aspirating from the region of the probe distal tip. The Eggers device uses the irrigant flow to provide a return path to a return electrode recessed axially a distance away from the active electrode(s).

The placement and volume of aspiration flow through an electrosurgical instrument in the region of an active electrode, or even through the active electrode, may adversely affect the performance of the instrument. Electrosurgery, particularly procedures in which tissue is vaporized, is a thermal process. Aspiration which draws fluid through or around the active electrode surfaces draws away process heat, thereby decreasing heating of the conductive irrigant in the region so as to decrease bubble production and ablative arcing. This makes the device less efficient thereby requiring increased power to achieve acceptable performance.

SUMMARY OF THE INVENTION

It is accordingly an object of this invention to produce an electrosurgical probe which has high efficiency.

It is also an object of this invention to produce an electrosurgical probe which has a distal end of compact size.

It is further an object of this invention to produce an electrosurgical probe which may be used in applications in which the target tissue is not submerged in a conductive liquid.

It is additionally an object of this invention to produce an electrosurgical probe which has an irrigation means.

It is finally an object of this invention to produce an electrosurgical probe which has an aspiration means.

These and other objects are accomplished in the invention herein disclosed which is an advanced, high efficiency, electrosurgical probe equipped with one or more additional metallic electrodes which are not connected directly to any part of power supply circuit. This electrode may contact the surrounding conducting liquid and/or tissue. The potential of this electrode is "floating" and is determined by the size and position of the electrode, the tissue type and properties, and the presence or absence of bodily fluids or externally supplied fluid. This "floating" electrode is mounted in such a way that one portion of the electrode is in close proximity to the probe tip, in the region of high potential. Another portion of the floating electrode is placed farther away, in a region of otherwise low potential. This low region may be in the conductive fluid, in contact with tissue, or both.

The floating electrode generates and concentrates high power density in the vicinity of the active region, and results in more efficient liquid heating, steam bubble formation and bubble trapping in this region. This increases the probe efficiency, which allows the surgeon to substantially decrease the applied RF power and thereby reduce the likelihood of patient burns and injury. The probe may be operated so that the portion of the floating electrode in close proximity to the active electrode has sufficient current density to produce vaporization of the liquid and arcing so as to vaporize tissue. Alternatively, the probe may be operated so that the floating electrode contacts tissue and portions of the floating electrode in contact with the tissue have sufficient current density to thermally coagulate blood vessels. This is particularly useful for achieving hemostasis in vascular tissue, such as, for instance, that present when performing tonsillectomies.

These innovative electrosurgical devices with floating electrodes may be very effective in other medical procedures other than evaporation (ablation), such as, for instance, for thermal treatments, lesion formation, tissue sculpting, and tissue "drilling", with or without externally supplied liquids.

The electrosurgical device herein disclosed is a probe which has a proximal portion forming a handle, and an elongated distal portion having at its distal end at least one active electrode and at least one floating electrode. The active electrode is connected via cabling and means within the handle portion to an electrosurgical generator. In a preferred embodiment, at least a portion of the distal-most portion of at least one floating electrode is in close proximity to at least one active electrode. In a further preferred embodiment, the elongated distal portion is tubular, having a first lumen connected via a means within the handle portion to an external irrigant source, and a second, dielectric tube having a second lumen disposed within the first lumen and connected via a means within the handle portion to an external vacuum source. Irrigant is supplied via the first lumen and means at the distal tip to the region between at least one active electrode and the portion of at least one floating electrode in close proximity to the active electrode. Liquid and ablation products are aspirated from the region of the probe tip by the second lumen and means at the distal tip.

In other embodiments, the probe has irrigation supplied to the probe tip via both lumens and no aspiration through the probe is used. In other embodiments, the irrigation is through the first or second lumen only. In further embodiments, the probe is equipped with aspiration but not irrigation, the irrigant being applied to the site by an external device.

Additional preferred embodiments include added features which enhance the probe efficiency, for example by increasing the rate of bubble generation when voltage is first applied to the probe.

In still other embodiments, the active electrode and floating electrode form an array of protuberances in which the active and floating electrodes are interspersed.

In yet other embodiments, the probe is configured for producing holes in tissue.

These and other objects and features of the invention will become more fully apparent when the following detailed description is read in conjunction with the accompanying figures and examples. However, it is to be understood that both the foregoing summary of the invention and the following detailed description are of a preferred embodiment, and not restrictive of the invention or other alternate embodiments of the invention.

BRIEF DESCRIPTION OF THE DRAWINGS

FIG. 4 is a plan view of the objects of FIG. 3.

FIG. 5 is a side elevational sectional view of the objects of FIG. 3 at location A-A of FIG. 4.

FIG. 6 is a side elevational view of the objects of FIG. 3.

FIG. 7 is a distal end view of the objects of FIG. 3.

FIG. 19b is an auxiliary sectional view at location C-C of FIG. 19a.

DETAILED DESCRIPTION OF THE PREFERRED EMBODIMENTS

Figure 1:
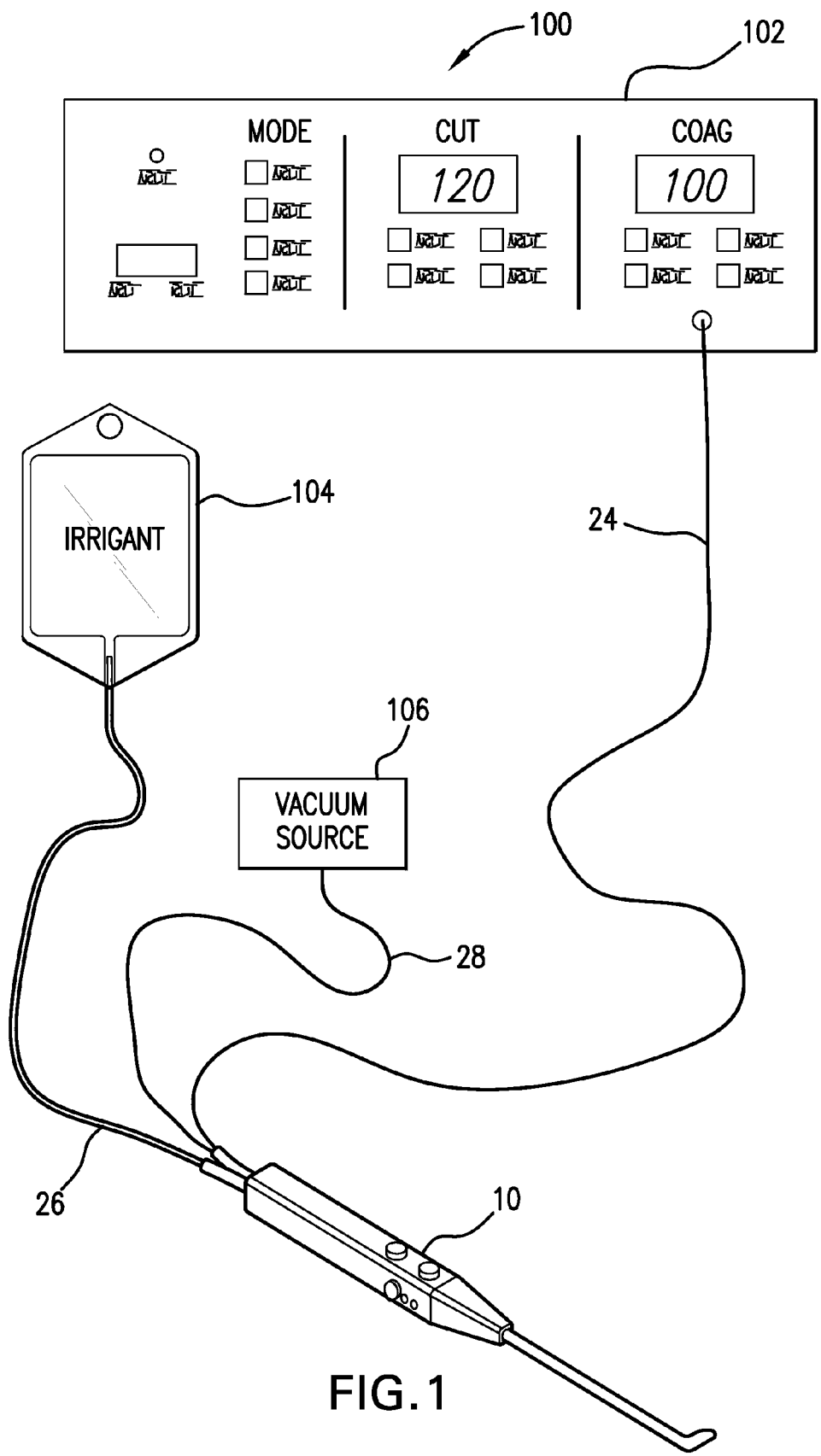
FIG. 1 shows an electrosurgical system formed in accordance with the principles of this invention.

The words "a", "an", and "the" as used herein mean "at least one" unless otherwise specifically indicated.

Unless otherwise defined, all technical and scientific terms used herein have the same meaning as commonly understood by one of ordinary skill in the art to which this invention belongs. In case of conflict, the present specification, including definitions, will control.

An electrosurgical probe is a metallic electrode coated with dielectric except for an exposed portion at the electrode tip. This tip is an active element of the probe. When placed into conductive liquid-tissue media and energized, the probe induces electrical current in the conducting liquid and nearby tissue. This current deposits energy into the liquid and tissue raising their temperatures and creating the desired clinical effect. The highest energy deposition is in close proximity to the tip where current density is largest.

Power density in close proximity of the tip depends primarily on the applied voltage, the shape and size of the exposed portion of the electrode, and surrounding liquid/tissue electrical conductivity. Also it is affected by the return current electrode size, shape, and position. In general, positioning the return electrode in closer proximity to the active electrode increases the power density in the region near the electrode tip.

In the case of a monopolar probe, the return current is collected by a large return electrode (sometimes called dispersive electrode or return pad) placed on the patient's body far away from the probe tip. The power concentration capability of a monopolar probe is determined by the shape of the exposed electrode: the smaller and sharper the tip is, the better its power concentration capability.

In the case of bipolar probes the return current electrode is placed in moderate proximity to the active electrode (generally from 1 to 10 mm). Some additional power concentration takes place in comparison with the monopolar probe with the same shape of active electrode. The power concentration capability can be controlled additionally by the shape and position of the return electrode. Decreasing the distance between the return electrode and the active electrode increases the power concentration. A problem arises when the probe is generating sparks. (Recall that this is the goal of probe operation in ablation-tissue evaporation or cutting, for example). If the return electrode is placed sufficiently close to the tip to achieve a substantial increase of power concentration, the breakdown (arcing within bubbles) takes place between the tip and return electrode. The spark conductive channel connects the active electrode to the return current electrode and the power supply is loaded directly by the spark. Usually this leads to extra high-energy deposition in the spark between metallic electrodes resulting in localized melting and vaporization of the electrodes themselves. This results in shorting of the power supply and destruction of both the active and return electrodes with little clinical benefit to the patient.

A good bipolar probe design must avoid arcing between the active and return electrodes. Usually this is achieved by placing the return electrode a sufficiently large distance away from the active electrode to prevent direct breakdown between electrodes. Nevertheless, periodic arcing may take place so that both electrodes are eroded and eventually destroyed, especially in an aggressive mode of operation. Therefore, the additional degree of power concentration achievable by bipolar probes is severely limited.

The electrosurgical device of the present invention has one or more additional metallic electrodes which are not connected directly to any part of the power supply circuit, and therefore are called "floating". These floating electrodes are in contact with the tissue and/or liquid in proximity to the active electrode. The electrical potential of these additional electrodes is not fixed, but rather is "floating" and is determined by size and position of the electrode and the electrical conductivity of the tissue and/or liquid surrounding the distal end of the device. This electrode is positioned in such a way that one end of the electrode is in close proximity to the active electrode. Another portion of the floating electrode is positioned in a region of low potential in the liquid and/or tissue. The addition of this floating potential electrode thereby substantially modifies the electrical field distribution, and energy deposition, in the vicinity of the active electrode without the possibility of electrode destruction since the floating electrode is not directly connected to the electrical power supply.

In the absence of sparking (arcing within bubbles) this electrode increases power density in the vicinity of the probe tip. This is because the floating electrode extends from a high potential region (near the active electrode), to a region with low potential (farther from the active electrode), and "shorts" these points together. The probe floating potential will be in between the potentials of these points. The presence of the electrode decreases the potential near the active electrode, therefore increasing the electric field, current and power density in the region near the active electrode. A floating electrode works about the same way as any extended conductive object in the electrostatic field. The higher power density results in more efficient liquid heating and steam bubble formation, which allows one to decrease the power applied to probe for a given effect. In the presence of the "floating" electrode more sparks are generated in the active region, since this region is larger. Bubble trapping (the retention of bubbles in selected areas to insulate these areas for improved ablator efficiency) is greatly enhanced with proper design of the floating electrode, insulator and the active electrode.

Sparks are an active element of an electrosurgical process. A spark is generated in a steam bubble if the bubble field (voltage difference across a bubble) is sufficient for breakdown. Usually sparks are generated in bubbles that are close to the active electrode of the probe because current density and field intensity are largest in this region.

The breakdown or spark inside a bubble is an electrically conductive channel of partly ionized pressurized gas. This medium is called highly collisional plasma. The basic property of this plasma is that the conductivity is proportional to the plasma density. Higher plasma temperatures are associated with higher ionization rates, plasma densities and conductivity.

Usually energy is deposited into highly collisional plasmas by electric current driven by voltage applied to electrodes at the ends of a plasma channel. In the case of a plasma channel formed inside of a bubble, the inner parts of the bubble surface with the largest voltage difference act as the electrodes to which the channel is connected. Most frequently, but not always, one of these electrodes is a metallic surface of the active electrode and the other is the opposite surface of the bubble or the surface of the tissue.

Electrically, the plasma channel is characterized by its impedance. The efficiency of energy deposition strongly depends on the ratio between the plasma channel and the power supply impedance. Efficiency (the portion of applied energy deposited to the plasma) as high as 50% can be achieved for matched conditions in which the power supply impedance equals the spark (plasma channel) impedance. If the channel impedance is too large or too small, the power deposition in the plasma is decreased. The power source for the plasma channel formation is the step voltage created by current flow in the conductive liquid surrounding the bubble. The effective impedance of the power supply is of the same order as the impedance of liquid with dimensions of a bubble. That means that the maximum power deposited into the arc channel is on the order of the power deposited into a volume of the bubble size filled with liquid. Deviation of the channel impedance from its optimum value results in decreased power deposition into the channel. These principles are valid if at least one of the channel electrodes is the inner liquid surface of bubble.

The energy which is deposited to a plasma channel (spark) is determined by the energy density in the surrounding conductive liquid. As taught previously herein, the additional metallic "floating" electrode described in this patent application significantly increases the energy density in the region surrounding the active electrode. This makes it possible to substantially increase the power deposited into the spark. Since the floating electrode can be placed very close to the probe tip, the largest probability is for breakdown and plasma channel formation in the region between the two metallic electrodes—the active electrode and the floating potential electrode. The plasma channel current can now be supported not by a bubble size fraction of the induced current, but by a much larger volume of current flow that is determined by the size of floating electrode. This floating electrode additionally concentrates current delivered to the spark. The optimum spark current can be controlled by adjusting the size and position of the floating electrode. Arcing, then, can occur through bubbles between the active and floating electrodes, or from either electrode through bubbles in contact with that electrode.

In summary, the subject of this invention is an advanced, electrosurgical probe equipped with an additional "floating potential electrode". The floating electrode concentrates the power (i.e. increases the power density) in the active region, which leads to more efficient liquid heating, steam bubble formation, and spark generation in this region. Arcing occurs from the floating electrode as well as the active electrode resulting in a probe in which the distal tip has a "working" diameter equal to the "physical" diameter in the case of probes having a radial symmetry. This is in contrast to an electrically active area normally being only about 50% of the physical area of the device.

More particularly, the device herein disclosed is an electrosurgical probe having a proximal portion forming a handle and a distal portion having at least one active electrode and at least one floating electrode at its distal end. The active electrode is connected via a cable passing through the proximal handle portion to a suitable RF energy source. The elongated distal portion has at least one lumen for supplying conductive irrigant to the probe distal tip, and a means for aspirating vapor and liquid from the region of the probe distal tip.

The floating electrode favorably affects bubble formation and trapping, and therefore enhances the probe's performance. This results in high efficiency operation, allowing the surgeon to substantially decrease the applied RF power and thereby reduce the likelihood of patient burns and injury, while at the same time maintaining high performance operation.

The method of the present invention includes the step of positioning the electrosurgical probe adjacent to target tissue at a surgical site so that at least one of the active electrodes and at least a portion of at least one of the floating electrodes are in close proximity to the target tissue. Conductive irrigant is supplied to the probe distal tip in the region between the active electrode(s) and the target tissue, and between the portion of the floating electrode in close proximity to the tissue, and the tissue. Other portions of the floating electrode(s) may be in contact with target tissue, adjacent tissue, or conductive irrigant. Vacuum is supplied via means within the elongated distal portion to the probe distal tip so as to remove excess irrigant and ablation products. The probe is energized producing high current density and arcing in portions of the active electrode and floating electrode in close proximity to the target tissue. Lower density current flow from regions of the floating electrode(s) in contact with adjacent target tissue results in desiccation of the adjacent tissue so as to achieve hemostasis. While energized, the probe is moved across the target tissue with a brushing or sweeping motion, or intermittently energized for a brief period of time and repositioned so as to affect the target tissue.

In a preferred embodiment, the floating electrode is an annular ring surrounding a single active electrode having ribs formed in its surface, the floating and active electrodes being separated by a ceramic insulator. Irrigant is supplied to the region between the floating and active electrodes, and aspiration is via a single aspirating port in the distal surface of the active electrode. In another embodiment, features formed in the active electrode distal surface minimize aspiration flow between the ribs so as to improve ablator efficiency. In another embodiment, radial slots are formed in the distal surface of the floating electrode to allow improved irrigation of the region surrounding the probe distal tip, and to increase the current density at the floating electrode distal surface. In yet another embodiment intended for applications in which the probe is oriented more or less vertically with the distal end downward additional irrigant is supplied to the probe distal end via a flow path along the outer surface of the elongated distal portion from the handle portion. The flow path is established by selective application of hydrophilic and/or hydrophobic coatings. In still another embodiment, the active and floating electrodes have protrusions which are interspersed in an array, the floating electrode protrusions being affixed to a portion of the floating electrode which is in the low-potential region of the electric field. Another embodiment is configured so as to function as a "tissue drill".

The current invention is useful also for medical procedures in which tissue is thermally treated rather than removed by vaporization, such as, for instance, cardiology, oncology and treatment of tumors, sometimes referred to as lesion formation. In these applications the device is brought into close proximity, or contact, with tissue with or without the presence of externally applied conductive fluid at the site for thermal treatment. The voltage applied to the active electrode is reduced to a level which produces current densities insufficient for forming sparks and the associated bubbles. Tissue is heated to a desired temperature for a predetermined time sufficient for lesion formation. The floating electrode intensifies the electric field in the region surrounding the active electrode so as to produce a larger, more controlled and more uniform lesion.

Hereinafter, the present invention is described in more detail by reference to the exemplary embodiments. However, the following examples only illustrate aspects of the invention and in no way are intended to limit the scope of the present invention. As such, embodiments similar or equivalent to those described herein can be used in the practice or testing of the present invention.

Referring to the figures, FIG. 1 shows an electrosurgical system 100 formed in accordance with the principles of this invention. System 100 has an electrosurgical generator 102 connected via cable 24 to electrosurgical probe 10, an irrigant source 104 which supplies conductive liquid to probe 10 via tubing 26, and a vacuum source 106 connected via tubing 28 to probe 10.

Figure 2:
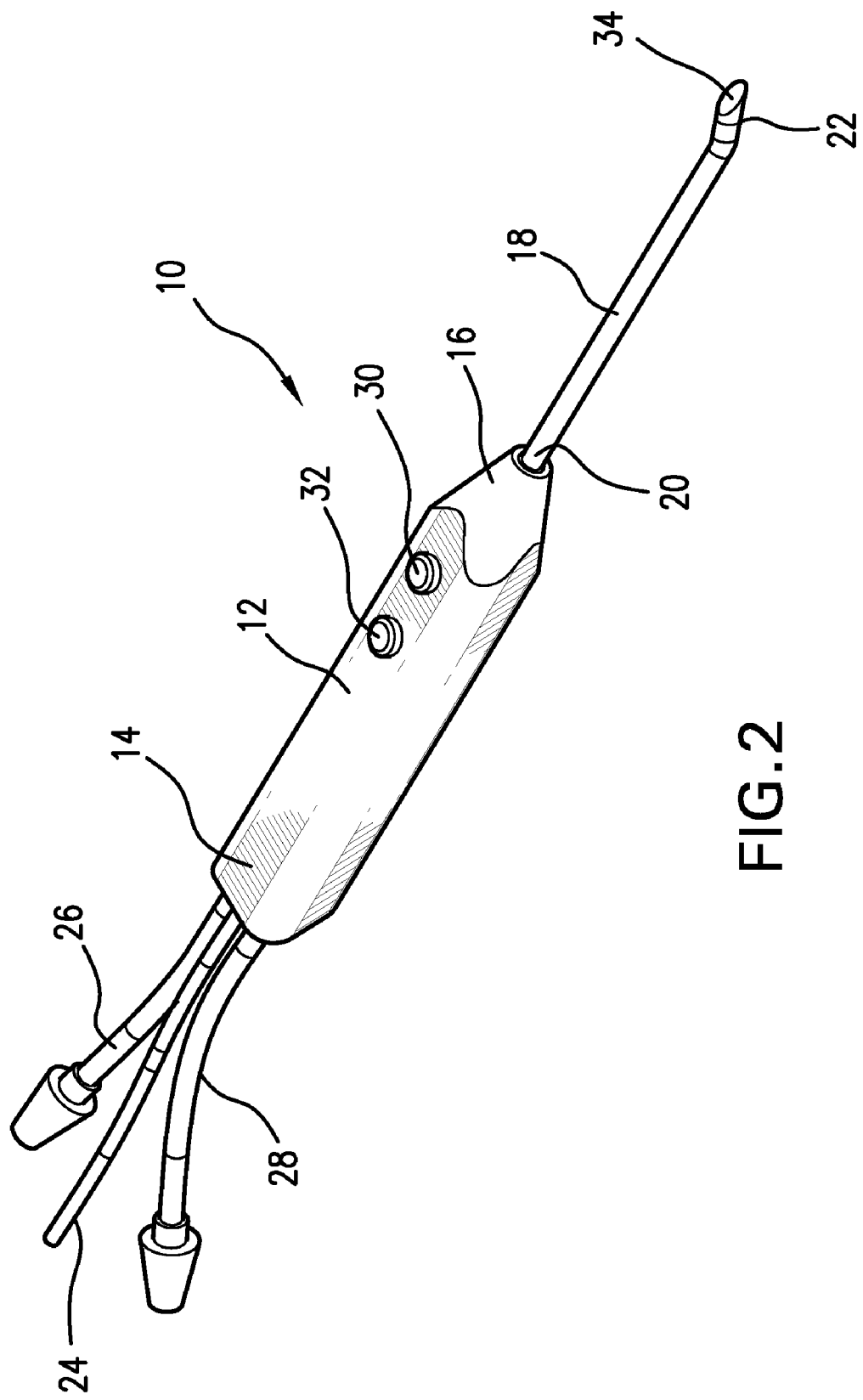
FIG. 2 shows an electrosurgical probe formed in accordance with the principles of this invention.
Figure 3:
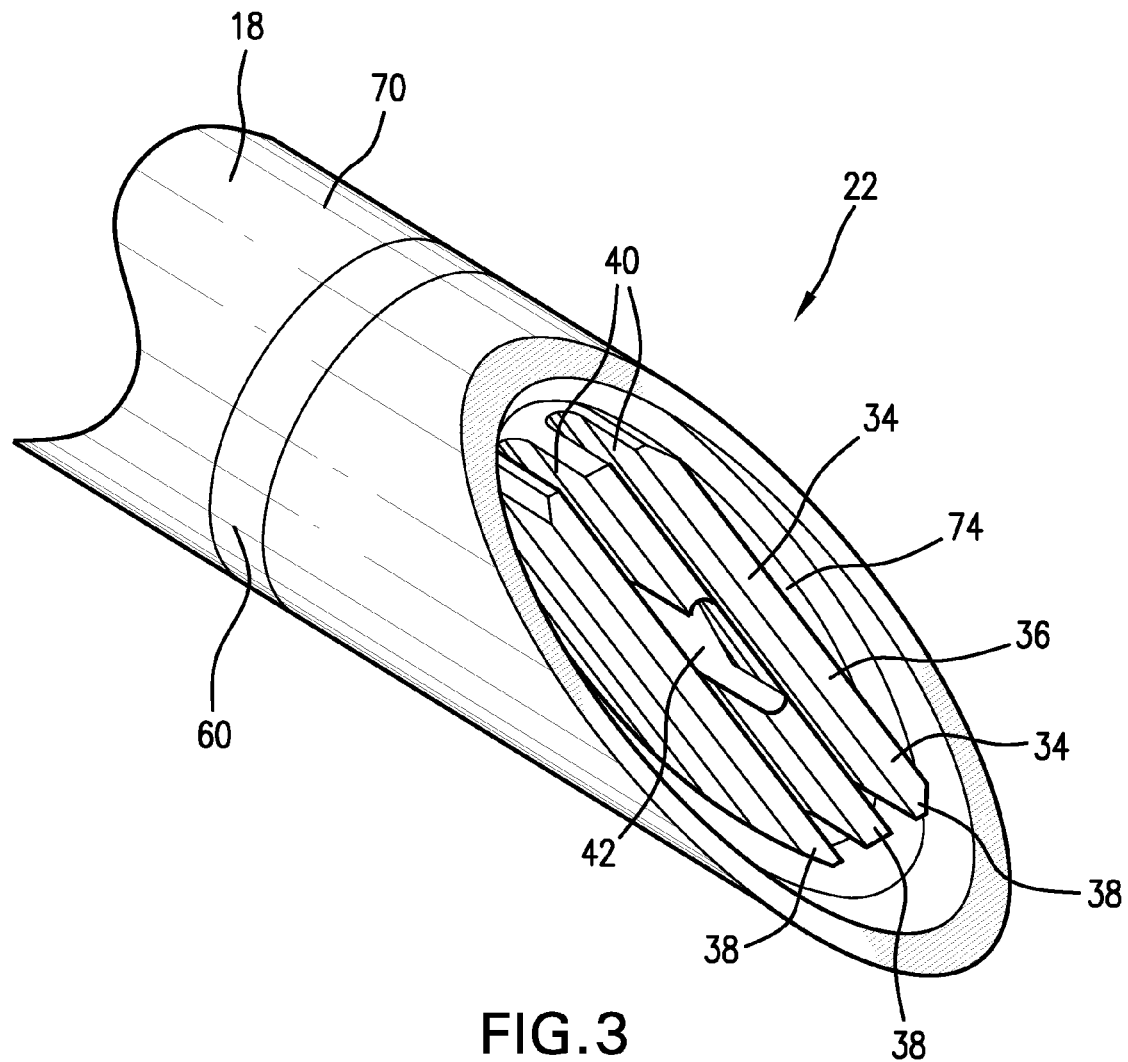
FIG. 3 is an expanded perspective view of the distal end of the object of FIG. 2.

As seen in FIG. 2, the electrosurgical instrument 10 formed in accordance with the principles of this invention has a proximal portion 12 forming a handle having a proximal end 14 and a distal end 16, and an elongated distal portion 18 having a proximal end 20 and a distal end 22. Proximal end 20 of distal portion 18 is rigidly affixed to distal end 16 of handle 20. Proximal end 14 of handle 12 has passing therefrom cable 24 which connects to electrosurgical unit 102 (FIG. 1), first tube 26 connects to irrigant source 104, and second tube 28 connects to vacuum source 106. Near distal end 16 of portion 12, first activation button 30 and second activation button 32 are connected via cable 24 to electrosurgical unit 102. Distal end 22 of elongated distal portion 18 comprises an active electrode 34.

Figure 8:
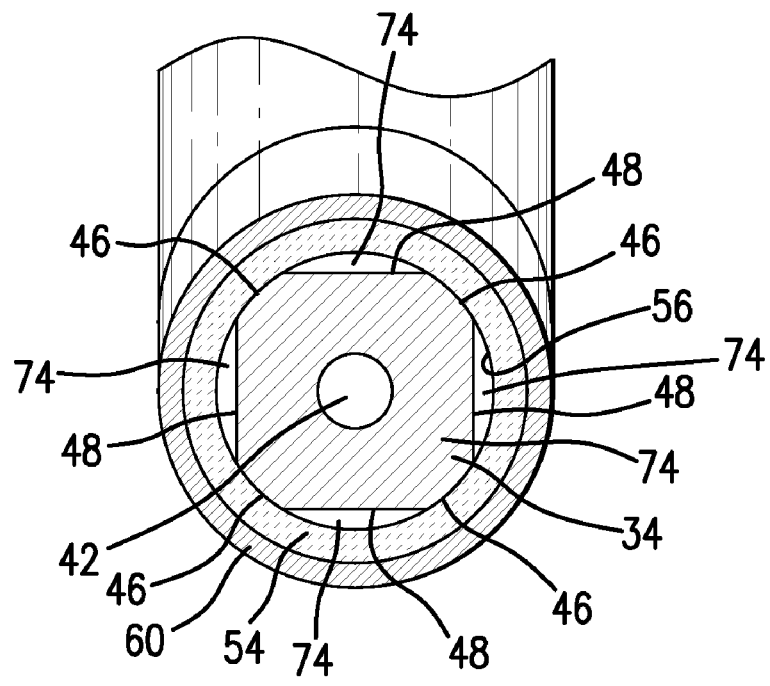
FIG. 8 is an axial sectional view of the objects of FIG. 3 at location A-A of FIG. 7.
Figure 9:
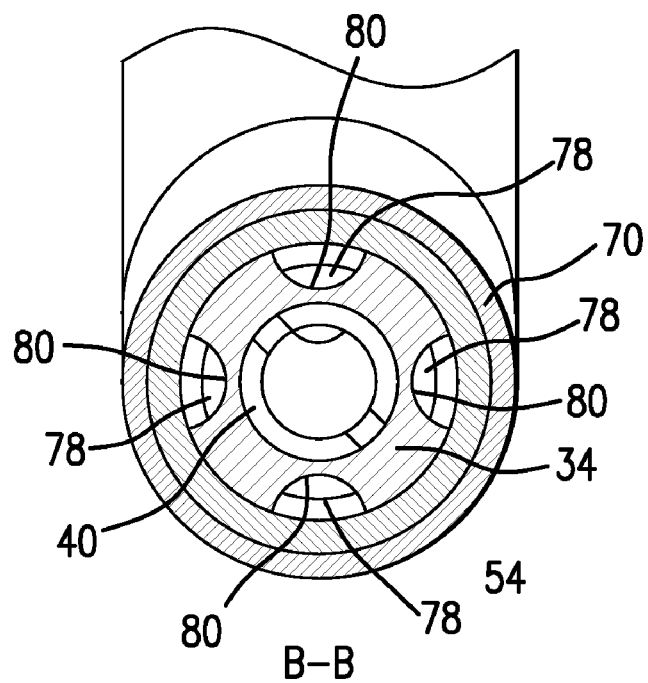
FIG. 9 is an axial sectional view of the objects of FIG. 3 at location B-B of FIG. 7.

Referring now to FIGS. 3 through 9 showing expanded view of distal end 22 of distal portion 18, active electrode 34 has an angled distal surface 36 forming a plurality of ribs 38 separated by grooves 40. Aspiration port 42 is connected by tube 44 and means within proximal portion 12, to second tube 28 (FIG. 2). As best seen in FIG. 8, when viewed axially electrode 34 has a cross-section having cylindrical portions 46 and planar portions 48. Proximal end 50 of electrode 34 is assembled to distal end 52 of outer tube 54, cylindrical portions 46 of electrode 34 locating in counterbore 56 of tube 54. Tubular insulator 60, formed of a suitable dielectric material, surrounds distal portion 62 of electrode 34. Floating electrode 64, made of a suitable metallic material, surrounds distal portion 58 of insulator 60, and is mounted thereto. Distal angled surface 66 of floating electrode 64 is more or less coplanar with surface 36 of electrode 34. Dielectric coating 70 surrounds the outer surface of outer tube 54 and proximal portion 72 of insulator 60. Passages 74 formed by cylindrical inner surface 76 of insulator 60 and planar surfaces 48 of active electrode 34 connect with lumen 78 of outer tube 54 via milled passage portions 80 of active electrode 34. Flow paths 82 formed by passages 74, milled passage portions 80 of active electrode 34, and lumen 78 of outer tube 54 connect via a means in proximal handle portion 12 to second tube 26 which is connected to irrigant source 104 (FIG. 1).

Figure 10:
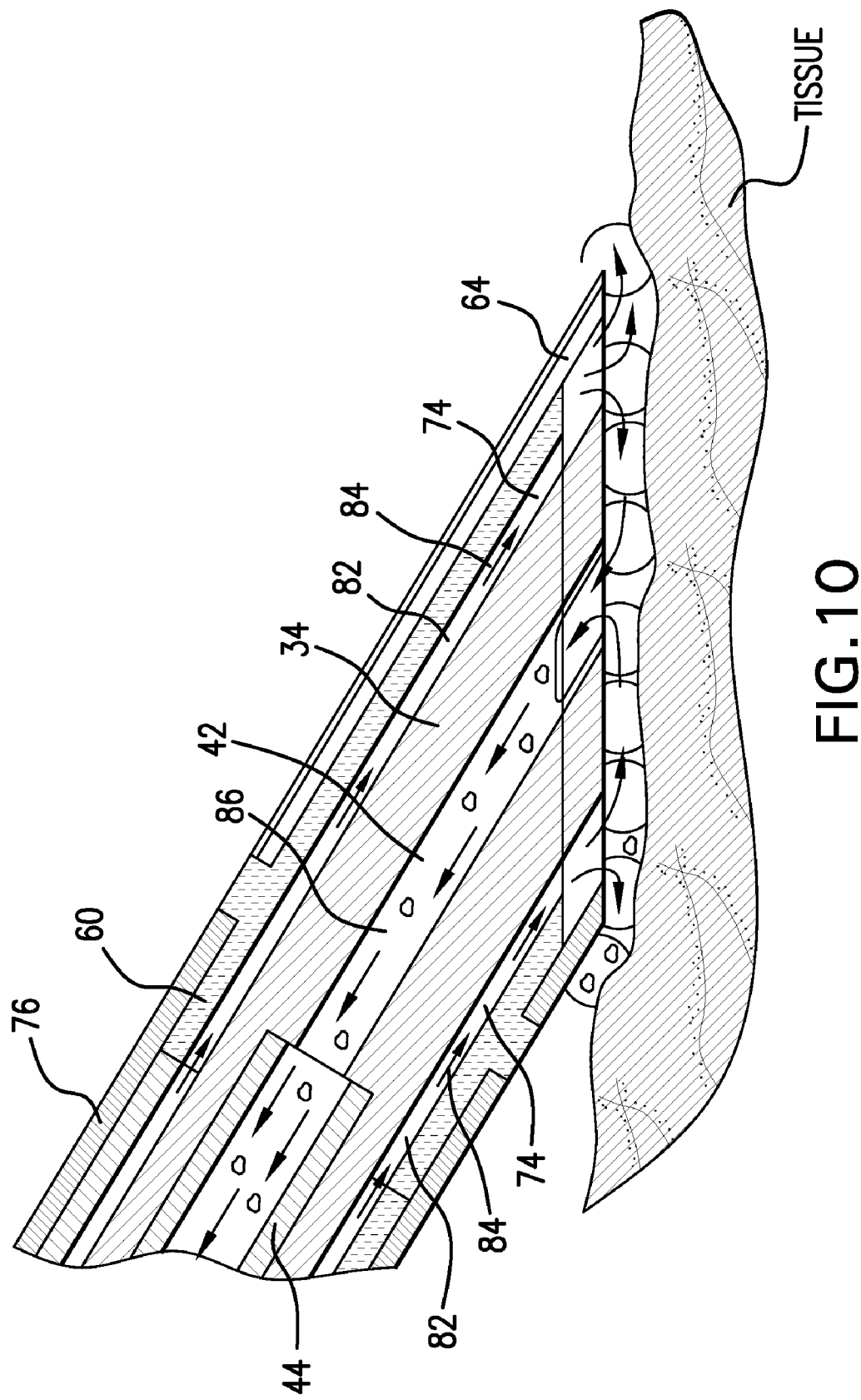
FIG. 10 is an expanded sectional view of the distal portion of the object of FIG. 2 during use.

Referring now to FIG. 10 showing instrument 10 in use, irrigant 84 supplied via flow paths 82 to passages 74 floods the region surrounding active electrode 34 and floating electrode 64. RF power supplied to active electrode 34, and conducted to floating electrode 64 by irrigant 84 causes boiling of the saline in contact with active electrode 34 and floating electrode 64, particularly at edges of the electrodes. Arcing through bubbles contacting either active electrode 34 or floating electrode 64 and tissue vaporizes the tissue in contact with the bubbles. Bubbles and debris from the ablation process (collectively 86) is aspirated from the region via aspiration port 42 by suction supplied by vacuum source 106 (FIG. 1) via second tube 28 (FIG. 2), means within proximal portion 12, and tube 44.

Figure 11:
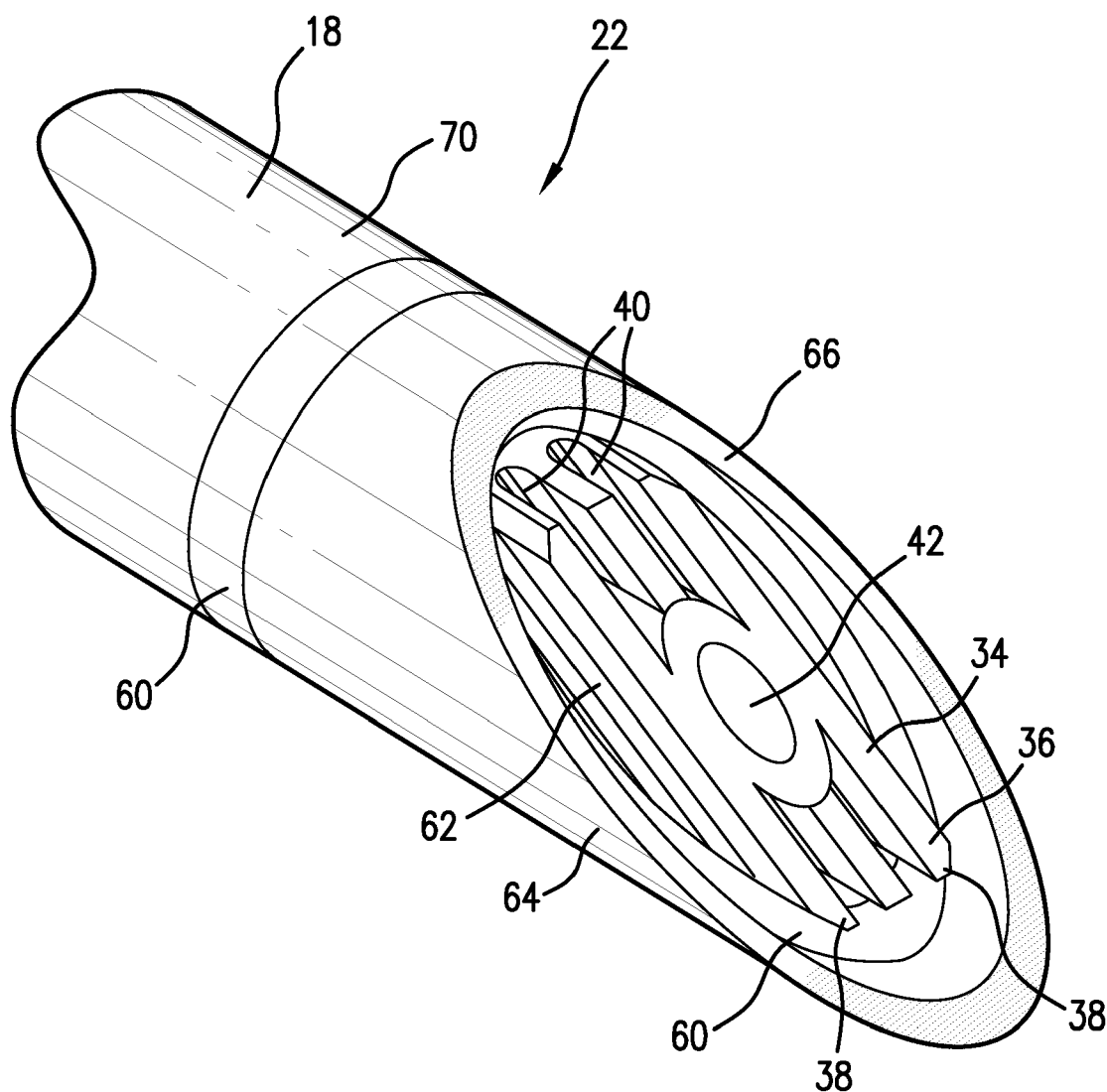
FIG. 11 is an expanded perspective view of the distal portion of an alternate embodiment.

An alternate embodiment, shown in FIG. 11, is identical to that shown in FIGS. 3 through 9 except that cylindrical portion 88 of active electrode 34 extends aspiration port 42 so that it is coplanar with surface 36 of electrode 34. Extending the aspiration port in this manner minimizes aspirating flow between ribs 38 in grooves 40 so as to minimize cooling of the ribs by the flow. This, in turn, increases the efficiency of the ablator since less process heat is removed by the aspiration flow.

Figure 12:
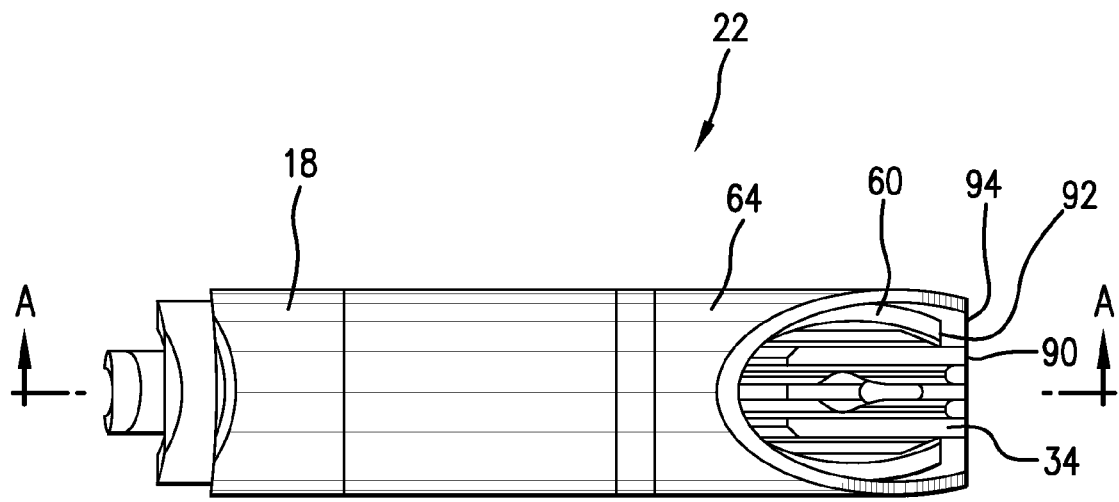
FIG. 12 is an expanded plan view of the distal portion of another embodiment.
Figure 13:
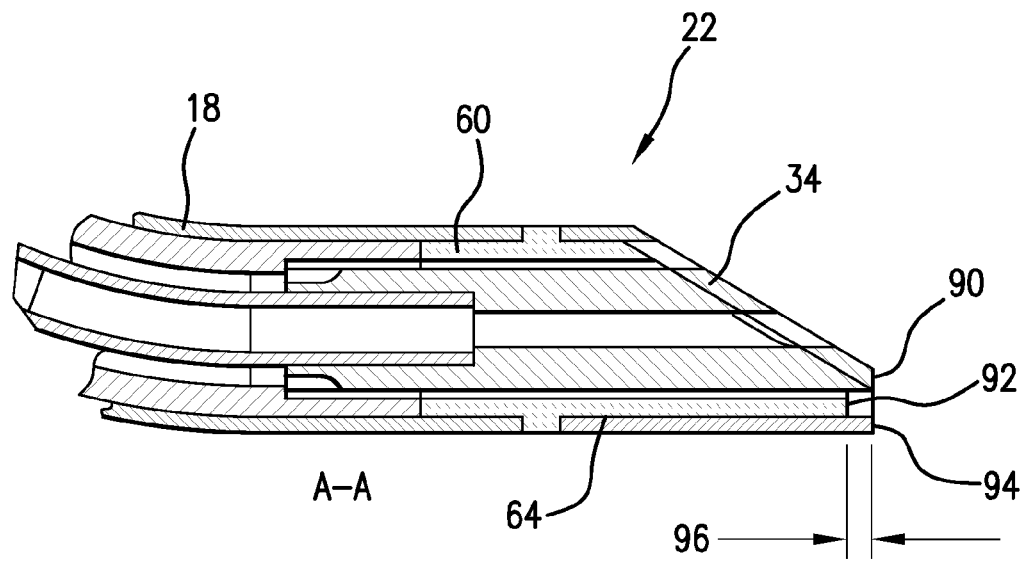
FIG. 13 is a side elevational sectional view of the objects of FIG. 12 at location A-A of FIG. 12.
Figure 14:
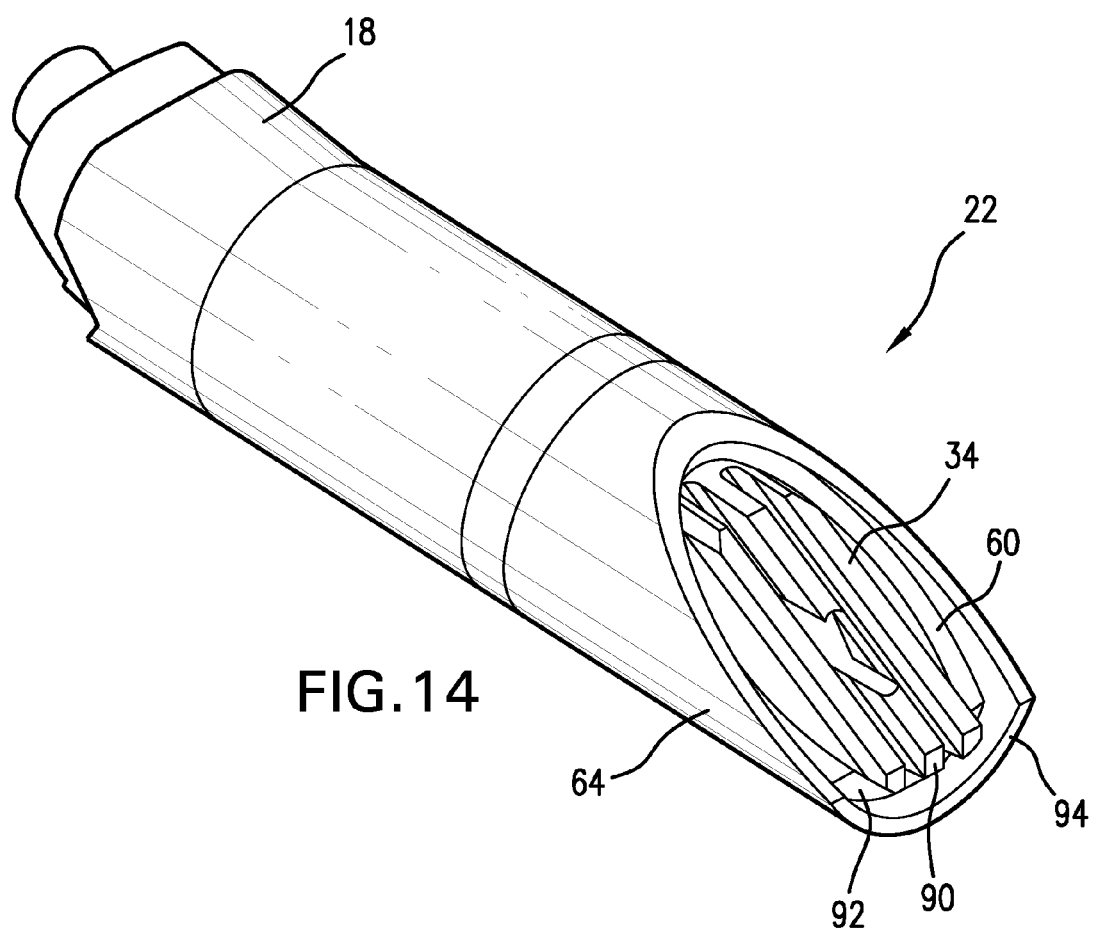
FIG. 14 is a perspective view of the objects of FIG. 12.

In another embodiment shown in FIGS. 12 through 14, active electrode 34, insulator 60 and floating electrode 64 are truncated so as to produce distal planar surface 90 on electrode 34, distal planar surface 92 on insulator 60, and distal planar surface 94 on floating electrode 64. Surfaces 90, 92 and 94 are normal to axis 91 of active electrode 34. Surface 90 and 94 are more or less coplanar. Surface 92 is recessed axially distance 96 from surfaces 90 and 94.

Figure 15:
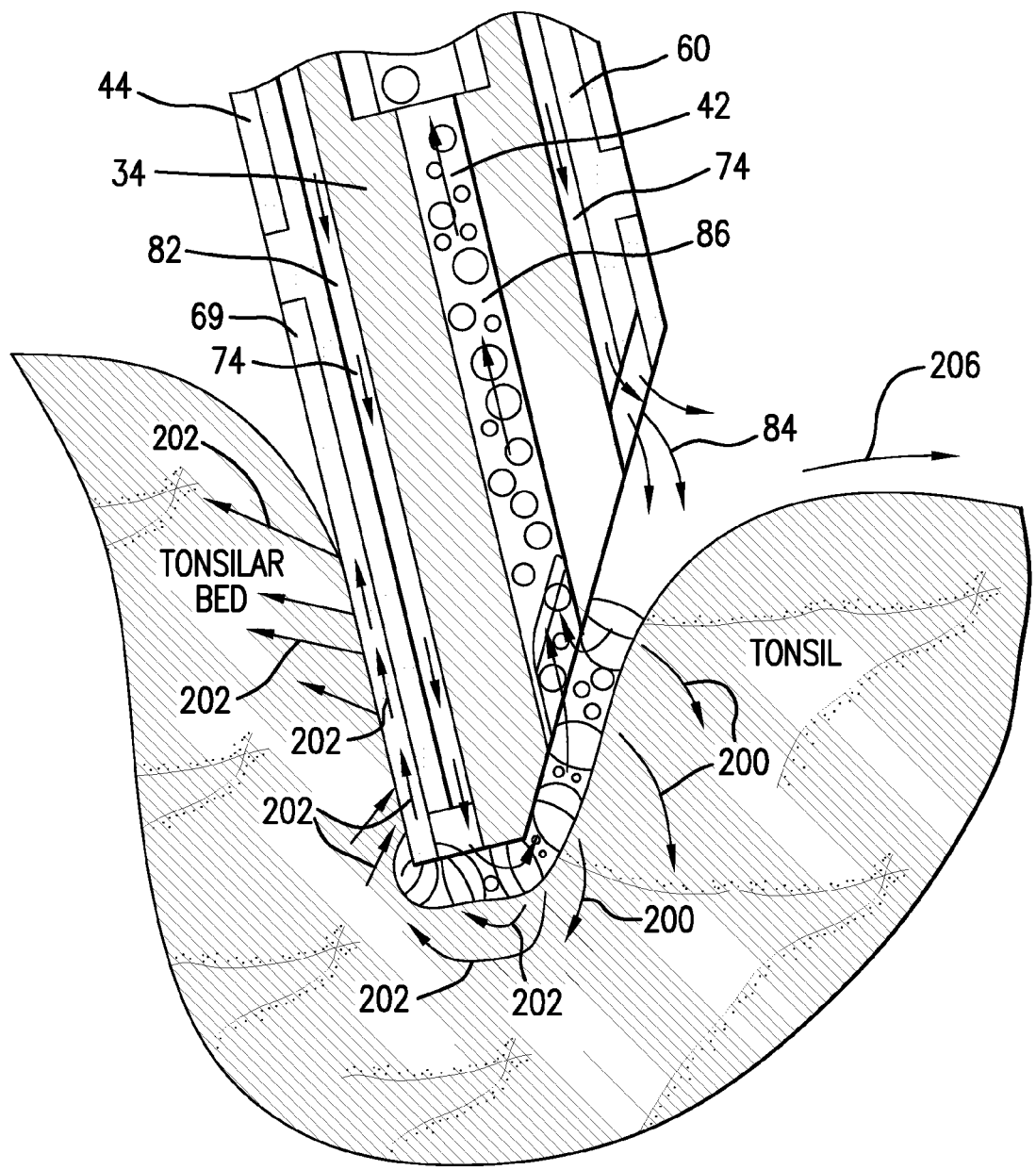
FIG. 15 is a side sectional view of the objects of FIG. 12 in use.

Referring now to FIG. 15, showing the embodiment of FIGS. 12 through 14 in use, for example, removing a tonsil from the tonsilar bed, the tonsil is pulled away from the tonsilar bed by a force applied to the tonsil by a grasping instrument. Instrument 10 is used to separate the tonsil from the tonsil bed by resecting tissue between the tonsil and the bed. As with the embodiment of FIG. 10, irrigant 84 supplied via flow paths 82 to passages 74 floods the region surrounding active electrode 34 and floating electrode 64. RF power supplied to active electrode 34, and conducted to floating electrode 64 by irrigant 84 causes boiling of the saline in contact with active electrode 34 and floating electrode 64, particularly at edges of the electrodes. Arcing through bubbles contacting either active electrode 34 or floating electrode 64 and tissue vaporizes the tissue in contact with the bubbles. Bubbles and debris from the ablation process (collectively 86) is aspirated from the region via aspiration port 42 by suction supplied by vacuum source 106 (FIG. 1) via second tube 28 (FIG. 2), means within proximal portion 12, and tube 40. Current 200 flows from the active electrode through the conductive liquid to the tissue through which it is conducted to the remotely affixed return electrode. A portion of the current 202 in the region in close proximity to floating electrode 64 and active electrode 34 flows from active electrode 34 through the conductive liquid to the portion of floating electrode 64 in the high-potential part of the electric field. This current 202 then flows through floating electrode 64 to a lower potential part of floating electrode 64, and from there through conductive liquid and tissue in contact with electrode 64 to the return electrode. Current density in the high-potential region of the electric field adjacent to floating electrode 64 is high, generally sufficient to cause boiling of the conductive liquid at the surface of floating electrode 64 and arcs 204 within the bubbles formed. Some of current flow 202 between active electrode 34 and floating electrode 64 follows a path through bubbles formed at active electrode 34 to adjacent tissue thereby vaporizing the tissue, and from the tissue to floating electrode 64 by arcing within bubbles formed at floating electrode 64 thereby vaporizing additional tissue. Current density in the portion of floating electrode 64 in the lower-potential portion of the electric field is less than that in the high-potential region. The current density is insufficient to cause boiling of the saline and ablative arcing. It is, however, sufficient to cause desiccation of tissue in contact with floating electrode 64 so as to coagulate bleeders, particularly oozing surfaces such as those found in the region of the tonsils.

Referring yet to FIG. 15, a separation force 206 is applied to the tonsil. Distal end 22 of instrument 10 is brought into close proximity to the tonsil adjacent to the tonsil bed. Irrigation and aspiration are supplied to the distal region. The probe is briefly energized so that tissue is ablated in the region of active electrode 34 and floating electrode 64. The probe is repositioned to a new location and again briefly energized so as to vaporize additional tissue. Instrument 10 is advanced axially into the tissue while being repositioned laterally so as to vaporize a portion of the tonsil. Simultaneously, current flow from floating electrode 64 desiccates tissue in contact with electrode 64 so as to achieve and maintain hemostasis. When the tonsil is freed from the tonsil bed, additional tissue can be removed from the tonsil bed by reorienting instrument 10 so that surface 36 of active electrode 34 and surface 66 of floating electrode 64 are adjacent the tonsil bed. Tissue is then ablated (vaporized) from the site in the manner previously herein described (FIG. 10).

Figure 16:
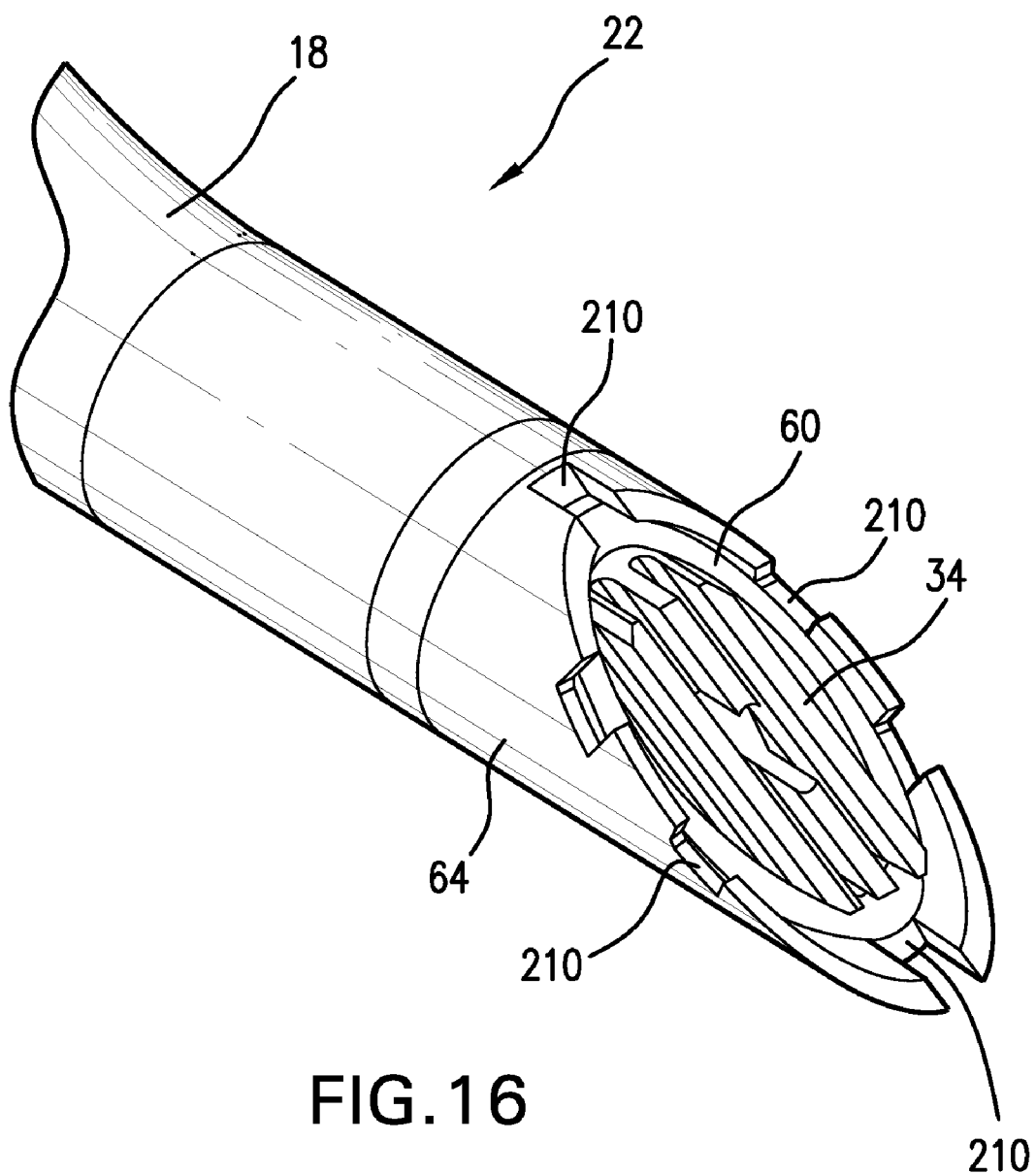
FIG. 16 is an expanded perspective view of the distal portion of an alternate embodiment.

In another embodiment shown in FIG. 16, floating electrode 64 has a plurality of slots 210 formed in angled surface 66 so as to allow enhanced irrigation of the region, irrigant flowing outwardly through the slots. By adjusting the number and width of slots 210 the portion of floating electrode 64 in the high-potential portion of the electric field can be reduced so as to achieve higher current densities at floating electrode 64. This causes enhanced bubble formation and ablative arcing at floating electrode 64.

Figure 17:
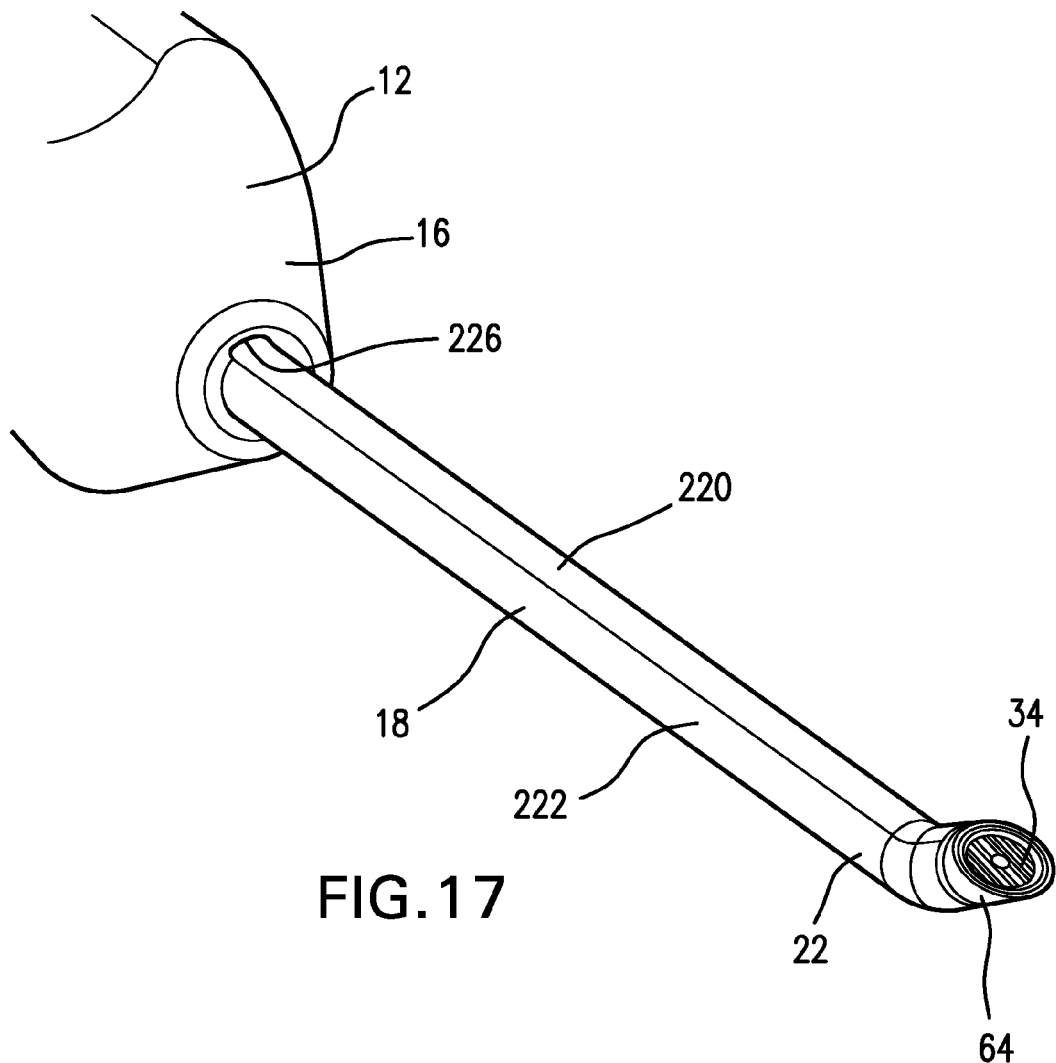
FIG. 17 is a perspective view of the distal portion of another alternate embodiment.
Figure 18:
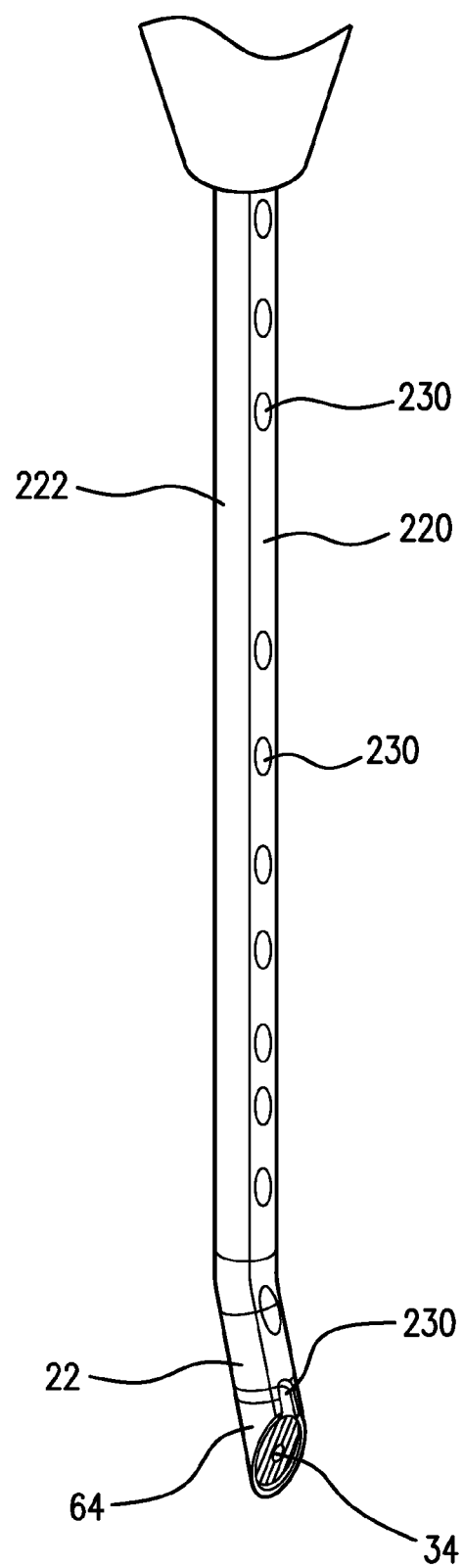
FIG. 18 is a perspective view of the objects of FIG. 17 positioned for use to show the irrigant flow path.

In yet another embodiment intended for use in applications such as that shown in FIG. 15 in which the probe is held more or less vertically irrigant flows down the outside of the elongated distal section. In the embodiment shown in FIG. 17, irrigant is supplied to distal end 22 of elongated distal portion 18 by a flow path 220 on the outer surface of dielectric coating 70. In one embodiment, the flow path is formed by a hydrophilic coating applied to path 220. In another embodiment path 220 is formed by a hydrophobic coating applied to portion 222 of the outer surface of dielectric coating 70 not part of path 220. In yet another embodiment path 220 is formed by a hydrophilic coating applied to path 220 and a hydrophobic coating applied to portion 222. Irrigation port 226 in distal end 16 of handle 12 supplies irrigant to proximal end 228 of path 220, the irrigant being supplied from an external source 104 via tube 26 (FIG. 1) and means within handle portion 12. In use (see FIG. 18), irrigant 230 flows from port 226 down path 220 to distal end 22 of elongated distal portion 18 where it provides conductive liquid for the ablation process. In some embodiments irrigant 230 supplements irrigant provided by the means previously herein described in previous embodiments. In other embodiments all irrigant is supplied via path 220.

Numerous changes may be made to the device and method without departing from the principles of the invention herein disclosed. For instance, in previous embodiments both suction and irrigation were supplied to distal end 22 of elongated portion 18. Other embodiments are anticipated in which irrigation is supplied to the surgical site via instrument 10 while aspiration of fluid and debris from the site is done by an external device. In these embodiments, irrigant is supplied in the manner previously herein described along path 82 (FIG. 10) and/or along path 220 (FIGS. 16 and 17) and may also be supplied along the path formed by port 42 and tube 44 used in previous embodiments for aspiration. Any combination of irrigation paths may be used.

Similarly, embodiments are anticipated in which irrigant is supplied by an external means to the site rather than by instrument 10 and aspiration is through instrument 10. Aspiration may be via the passage formed by port 42 and tube 44 (FIGS. 5 and 10) as in the previous embodiments or may be via path 82 (FIG. 10) used in previous embodiments for irrigation.

In the embodiment shown in FIGS. 3 through 9, distal angled surface 66 of floating electrode 64 is more or less coplanar with surface 36 of electrode 34. Under some circumstances, it may be advantageous to have surface 66 of floating electrode 64 displaced distally a predetermined distance from surface 36 of electrode 34. Accordingly embodiments having this distal offset between the surfaces is anticipated. In other embodiments portions of the distal-most surface of the floating electrode are displaced distally from the distal surface of the active electrode while other portions of the floating electrode surface are displaced proximally from the active electrode surface.

Figure 19A:
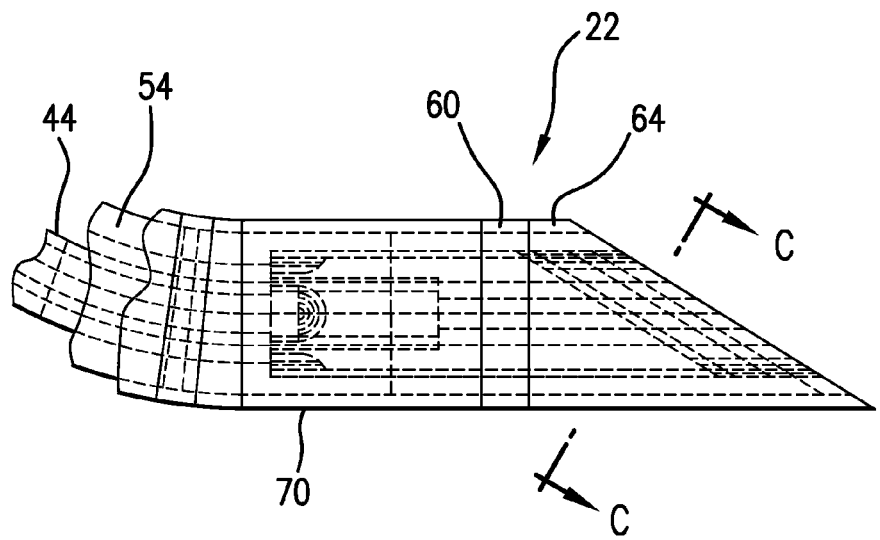
FIG. 19a is an expanded side elevational view of the distal portion of another alternate embodiment.
Figure 19B:
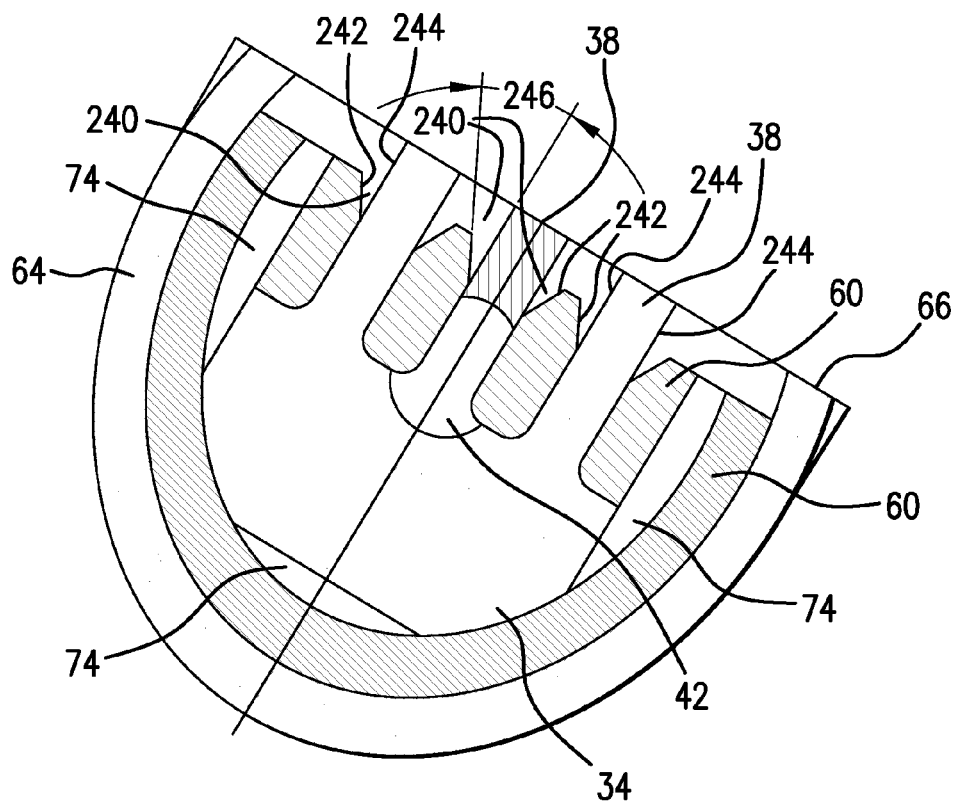
Figure 20A:
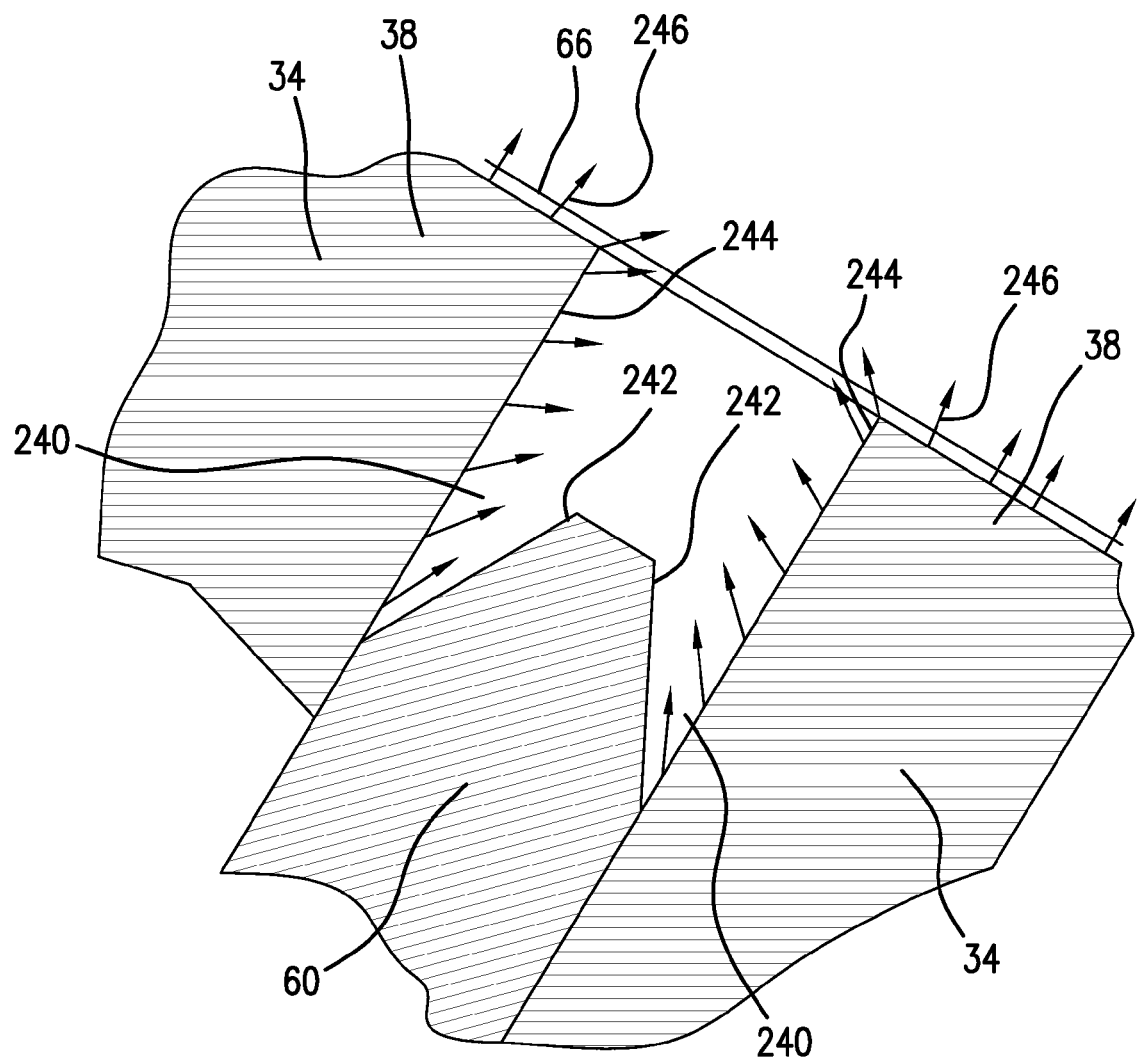
FIGS. 20a through 20e are an expanded view of an efficiency enhancing portion of the objects of FIG. 19b during use showing the function of the portion.
Figure 20B:
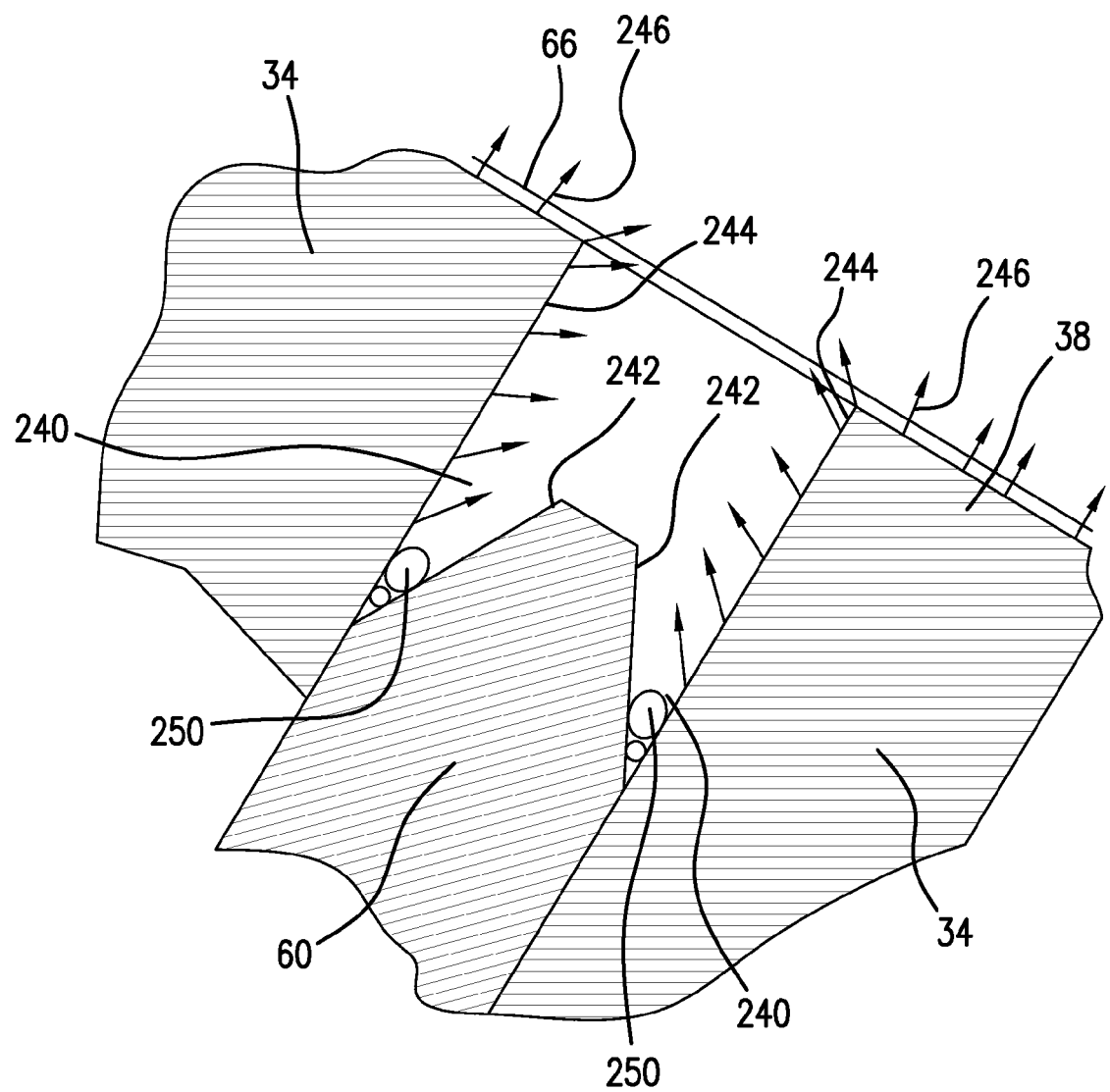
Figure 20C:
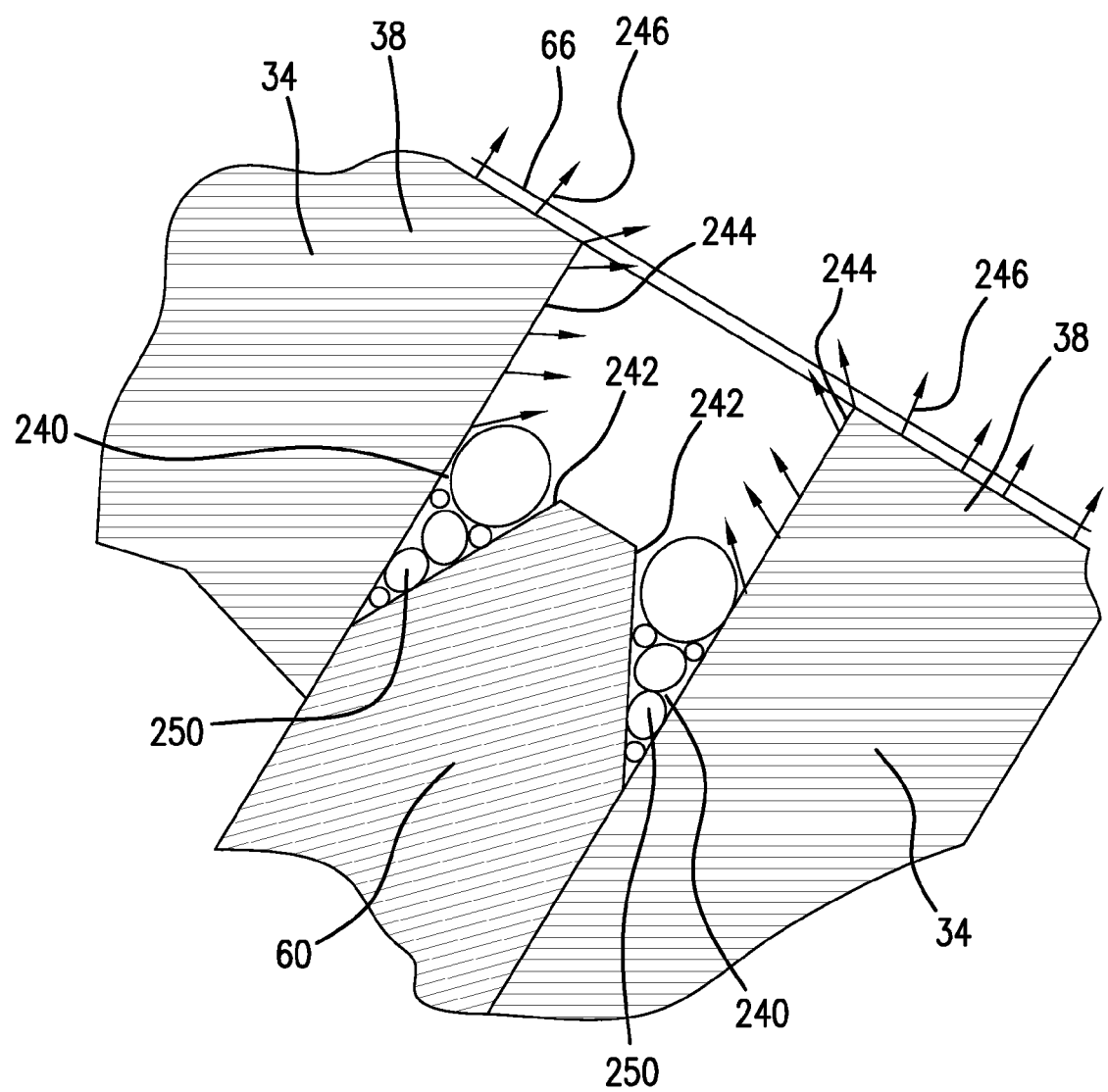
Figure 20D:
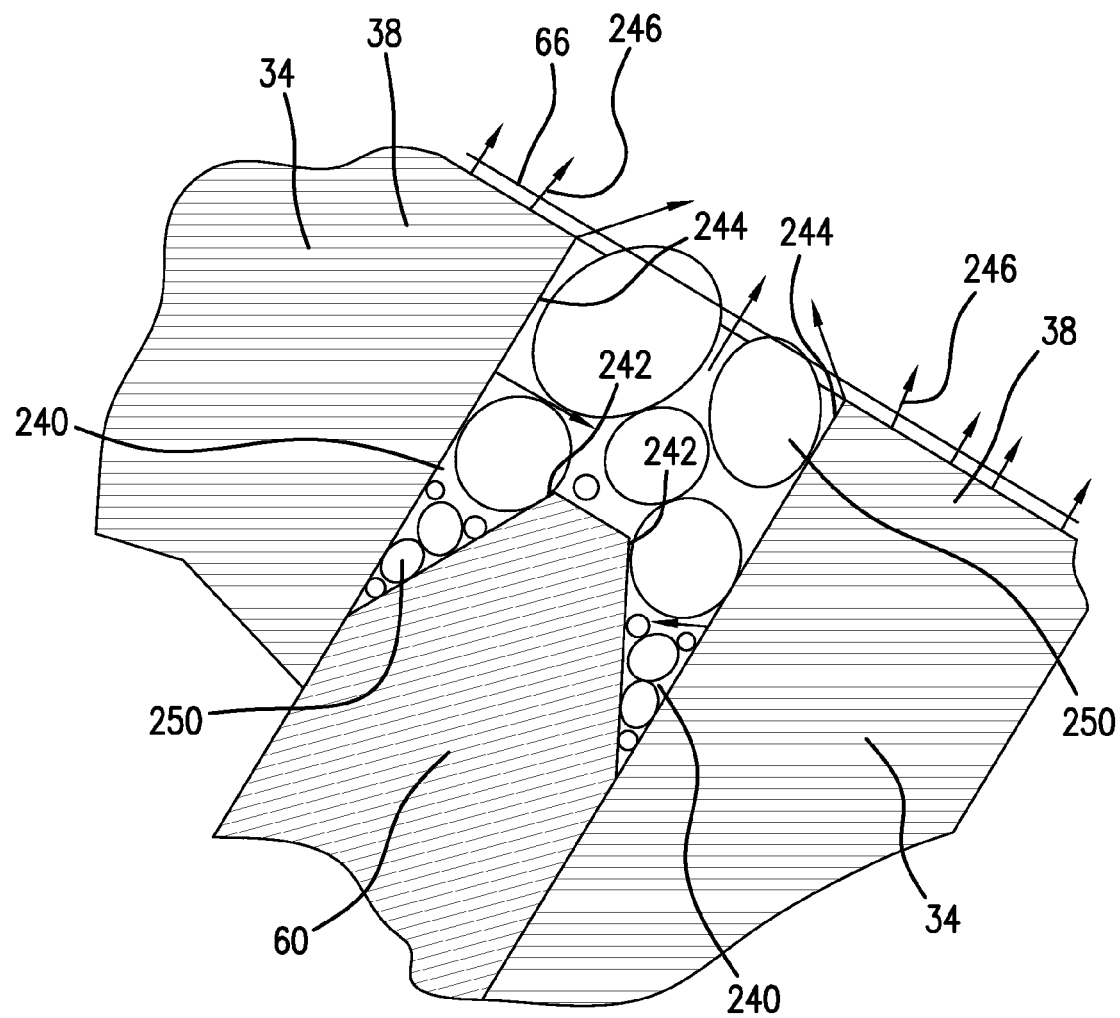
Figure 20E:
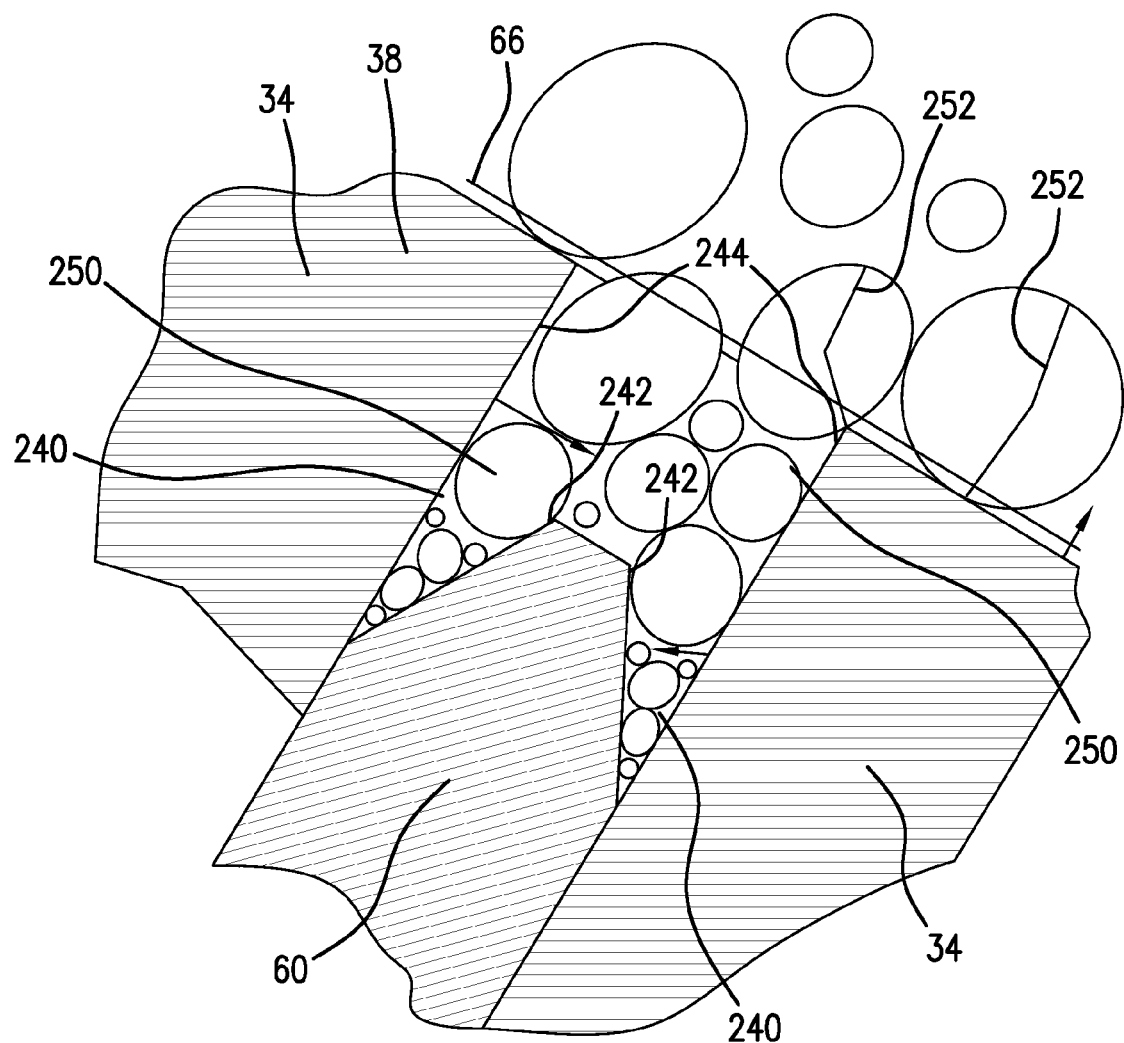

In another embodiment, features are formed in the distal-most surface of insulator 60, or in ribs 38 of active electrode 34 which enhance bubble formation and electrode efficiency. In one such embodiment, the distal portion 22 of which is shown in FIG. 19a, and a section view of which is show in FIG. 19b, grooves 240 are formed adjacent to ribs 38, grooves 240 having first walls 242 formed by angled surfaces of insulator 60, and second walls 244 formed by the lateral surfaces of ribs 38. Wall pairs 242 and 244 form an included angle 246 preferably in the range from 5 to 70 degrees, and more preferably in the range from 10 to 45 degrees. FIGS. 20a through 20e show an expanded view of ribs 38 and adjacent grooves 240 when voltage is first supplied to active electrode 34 while the assembly is submerged in conductive liquid. When voltage is first supplied (see FIG. 20a) current 246 flows from all uninsulated surfaces heating the adjacent liquid. Convection currents and fluid flow in the region surrounding active electrode 34 decreases the fluid temperatures in the region. Fluid within grooves 240 is not cooled by these mechanisms due to the narrow width of the grooves. Fluid cannot flow readily into and out of grooves 240. Fluid within grooves 240 heats at a higher rate than other fluid in other regions surrounding active electrode 34. As seen in FIG. 20b, showing the ribs 38 and grooves 240 a short time after FIG. 20a, heating of the liquid in grooves 240 causes boiling of the fluid in the grooves forming bubbles 250. After additional time has elapsed, as shown in FIG. 20c, grooves 240 are filled with bubbles 250 insulating surfaces 244 within grooves 240 so as to increase the impedance of the probe tip. When additional time has elapsed (see FIG. 20d), bubbles fill the region between ribs 38 insulating further surfaces 244. As seen in FIG. 20e, eventually bubbles 250 begin to cover the ablating surfaces of ribs 38 and arcing occurs within the bubbles. To summarize, liquid within grooves 240 heats at a higher rate than other fluid surrounding active electrode 34 thereby quickly creating bubbles 150 within grooves 240. The bubbles 150 generated insulate the lateral surfaces of the ribs 38 of electrode 34, and reach the distal-most surfaces of electrode 34 where acing occurs within the bubbles. In this manner grooves 240 increase the efficiency of ablator electrode 10.

Figure 21:
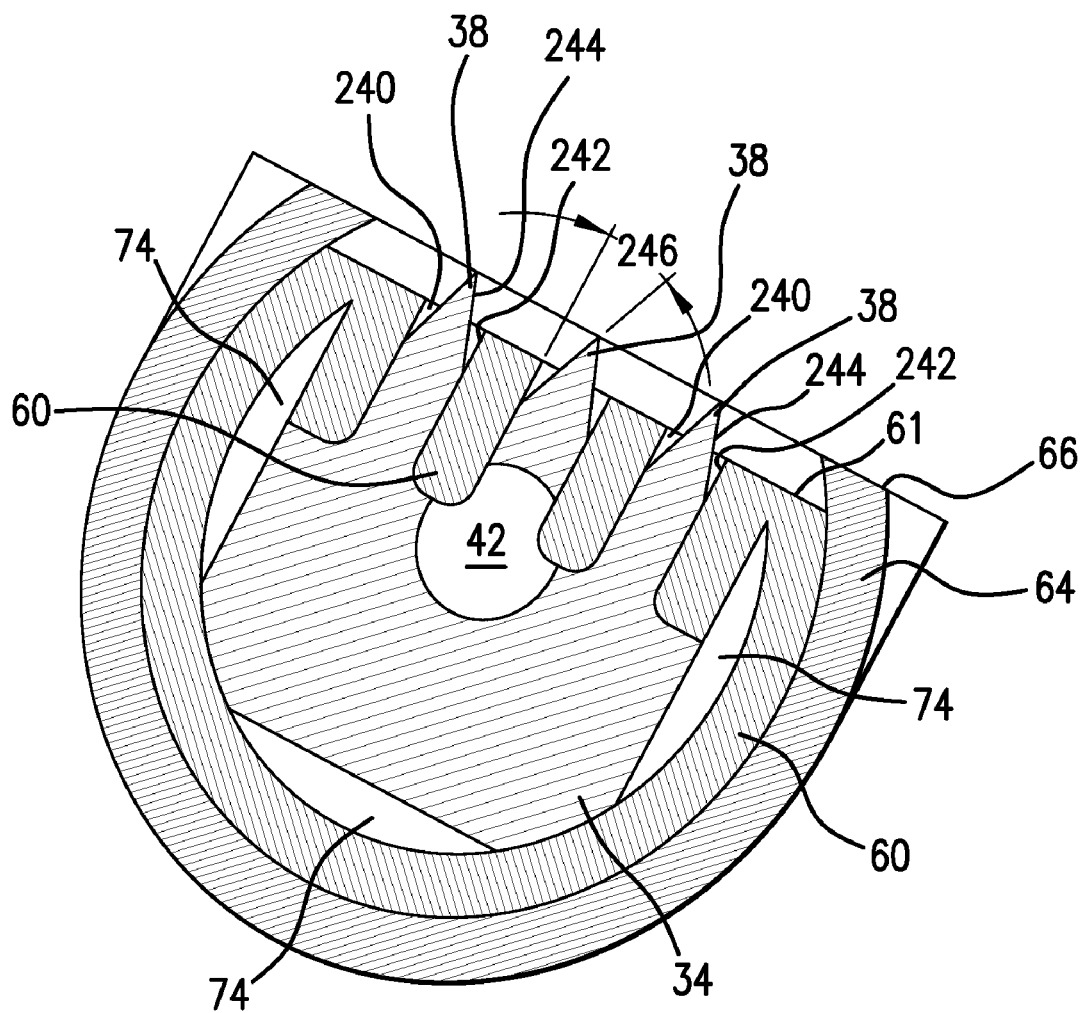
FIG. 21 is an auxiliary sectional view at location C-C of FIG. 19a of an alternate embodiment which is a modification of the embodiment of FIGS. 19a and 19b.

Another embodiment, having grooves 240 for the purpose of increasing electrode efficiency, is shown in section view in FIG. 21. Ribs 38 have a distal-most portion with a triangular cross-section, the proximal portion of the triangular portion being below distal surface 61 of insulator 60 so as to form grooves 240. Grooves 240 have an included angle 246 formed by surfaces 244 of ribs 38 and surfaces 242 of insulator 64. The embodiment of FIG. 21 functions in the same manner as that of FIGS. 19 and 20.

Figure 22:
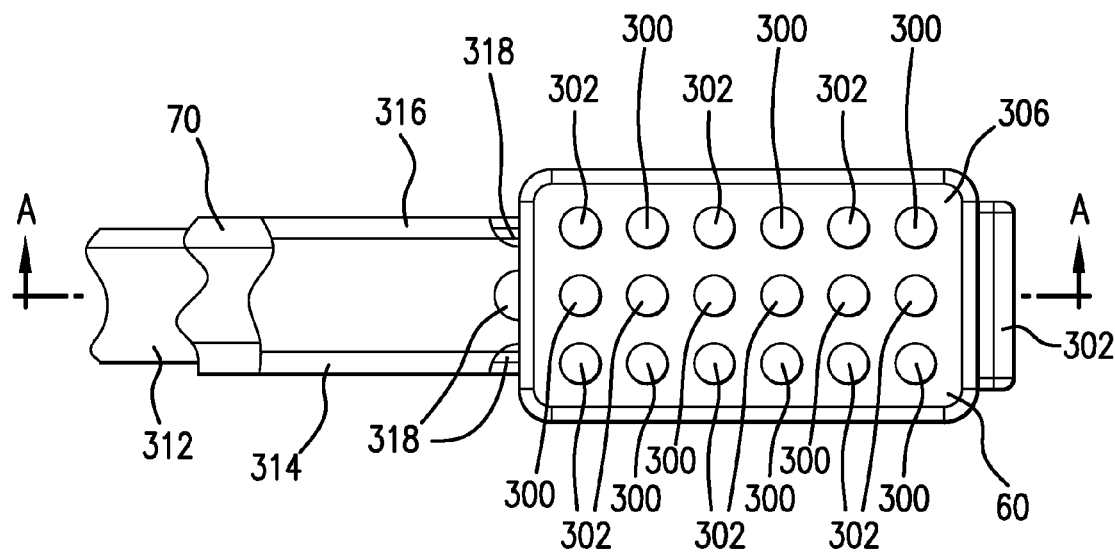
FIG. 22 is an expanded plan view of the distal portion of another alternate embodiment.
Figure 23:
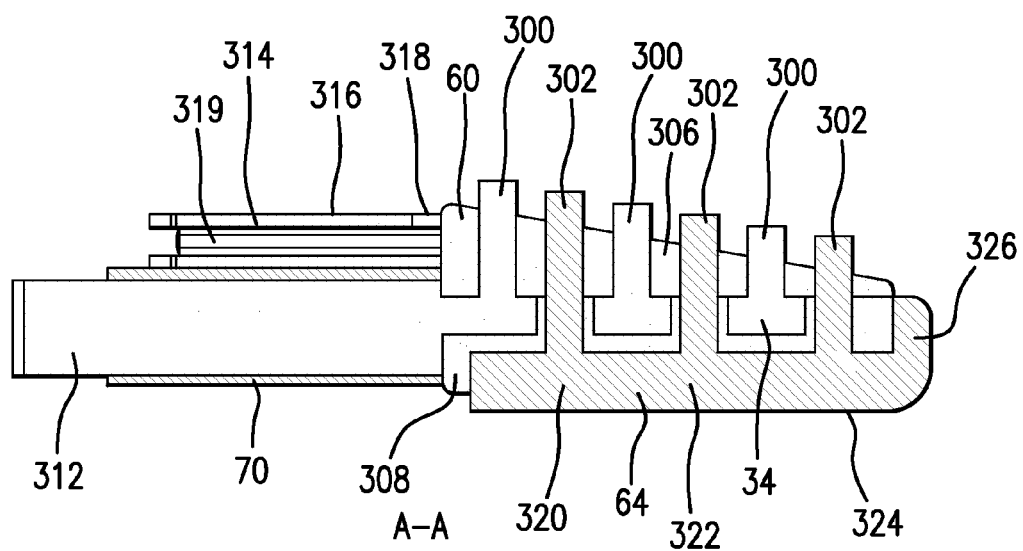
FIG. 23 is a side sectional view of the objects of FIG. 22 at location A-A of FIG. 22.
Figure 24:
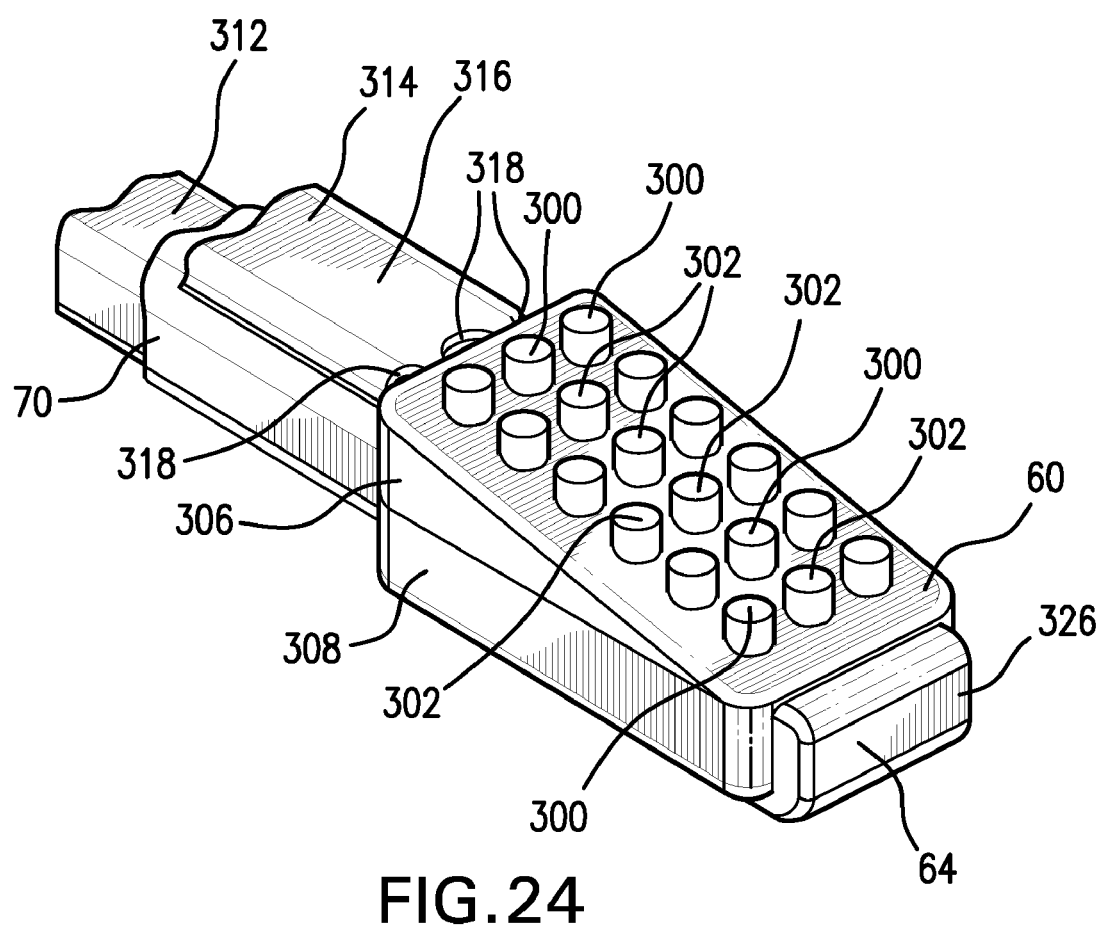
FIG. 24 is a perspective view of the objects of FIG. 22.

In yet another embodiment shown in FIGS. 22 through 24, active electrode 34 and floating electrode 64 form an array of protrusions. Active electrode 34 forms protrusions 300. Floating electrode 64 forms protrusions 302. Insulator 60 forms an assembly having a first portion 306 and a second portion 308, protrusions 302 and 304 protruding from surface 310 of first portion 306. Second portion 308 electrically isolates electrodes 34 and 64. Elongated conductive member 312 has at its distal end active electrode 34 and at its proximal end handle portion 12. Dielectric coating 70 covers member 312. Elongated tubular member 314, positioned adjacent to elongated member 312 and affixed thereto has a proximal end connected via means within handle portion 12 to a conductive irrigant source, and a distal end 316 having therein orifices 318 in communication with lumen 319. Floating electrode 64 has a proximal portion 320 forming protrusions 302, the portion 322 to which they are attached, and surface 324. Floating electrode 64 also has a distal portion 326.

Figure 25:
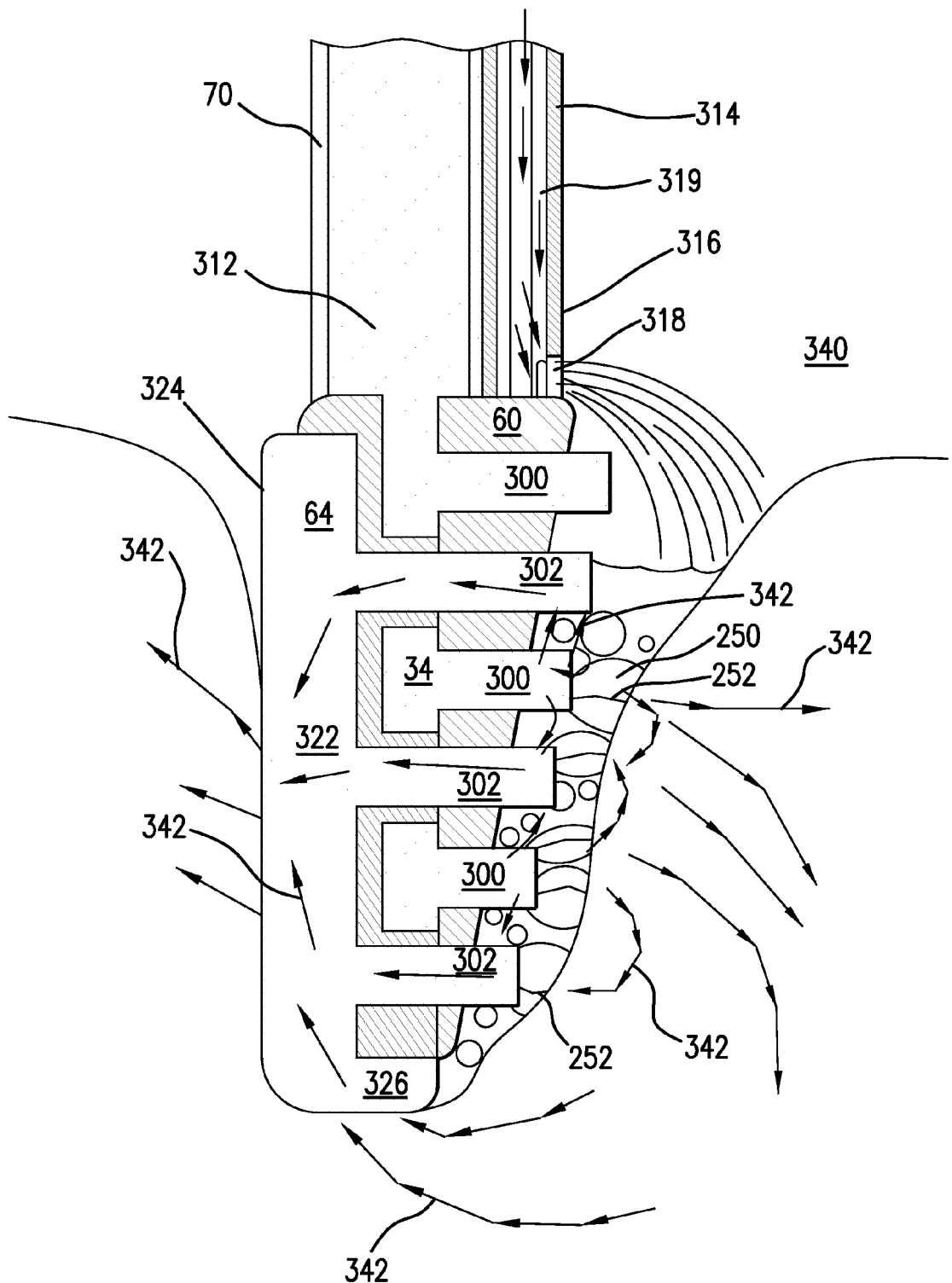
FIG. 25 is a sectional view of the object of FIG. 22 during use.

Referring now to FIG. 25, during use distal end 22 of ablator 10 is positioned such that at least one each of protrusions 300 of active electrode 34 and protrusions 302 of floating electrode 64 are in close proximity to the target tissue. Conductive irrigant 340 supplied by tubular member 314 via orifices 318 floods the region of the target tissue in close proximity to protrusions 300 and 302. Surface 324 of proximal portion 322 and/or distal portion 326 of floating electrode 64 are in contact with irrigant 340 and/or tissue in proximity to the target tissue. When voltage is supplied to active electrode 34, an electric field is established. Current 342 flows from protrusions 300 to the target tissue and from there to the remotely placed return electrode. Current also flows from protrusions 300 to protrusions 302 of floating electrode 64 in high potential regions of the electric field, through the floating electrode to lower potential regions of the electric field, and therefrom to the return electrode via tissue and conductive irrigant in contact with the portion of floating electrode 64 in low-potential regions of the electric field. Current flow through conductive irrigant 340 causes boiling of the irrigant resulting in bubbles 250, and arcs 252 within bubbles resulting in vaporization of tissue. This arcing occurs at protrusions 300 of active electrode 34 and also at some protrusions 302 of floating electrode 64 which are in high potential portions of the electric field. Current flow from the portions of floating electrode 64 in the lower-potential region of the electric field, particularly from surface 324, does not have sufficient density to form bubbles resulting in arcing; however, the current density is sufficient to cause heating of adjacent fluid and tissue so as to achieve and maintain hemostasis.

Figure 26:
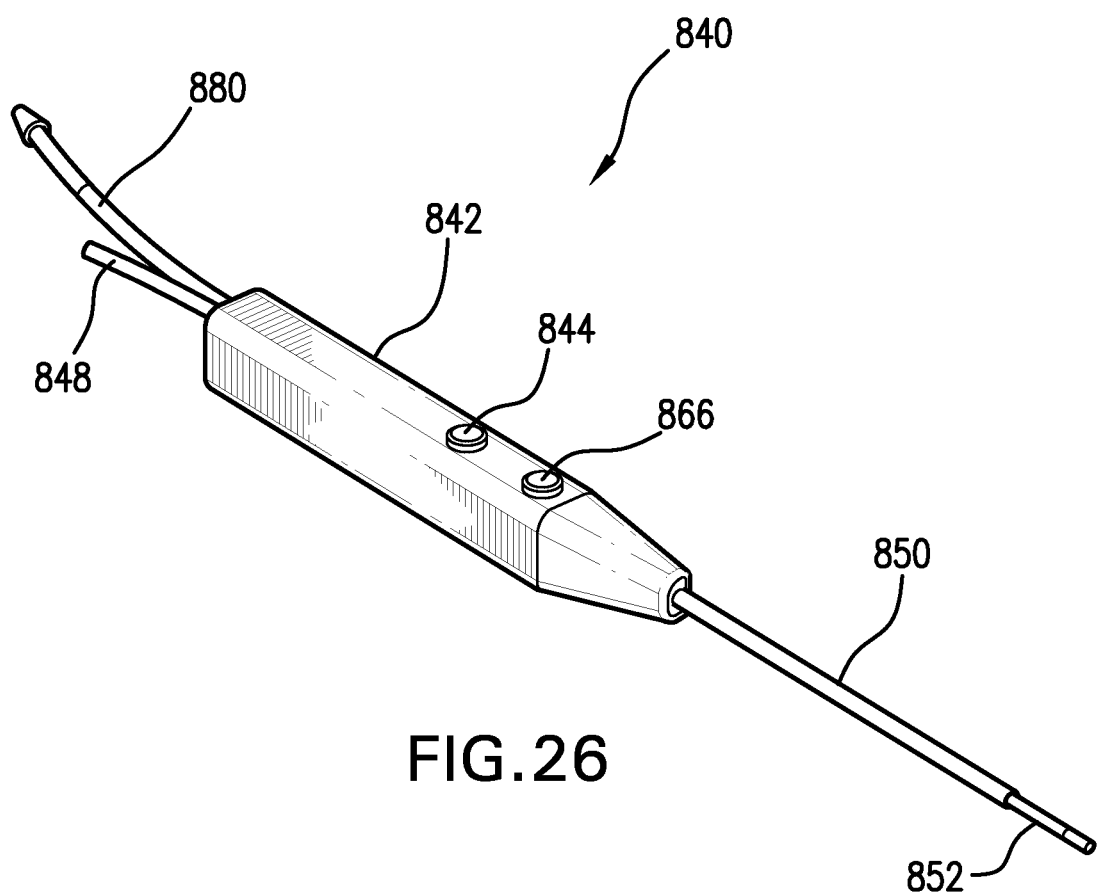
FIG. 26 is a perspective view of another embodiment for forming holes in tissue.
Figure 27:
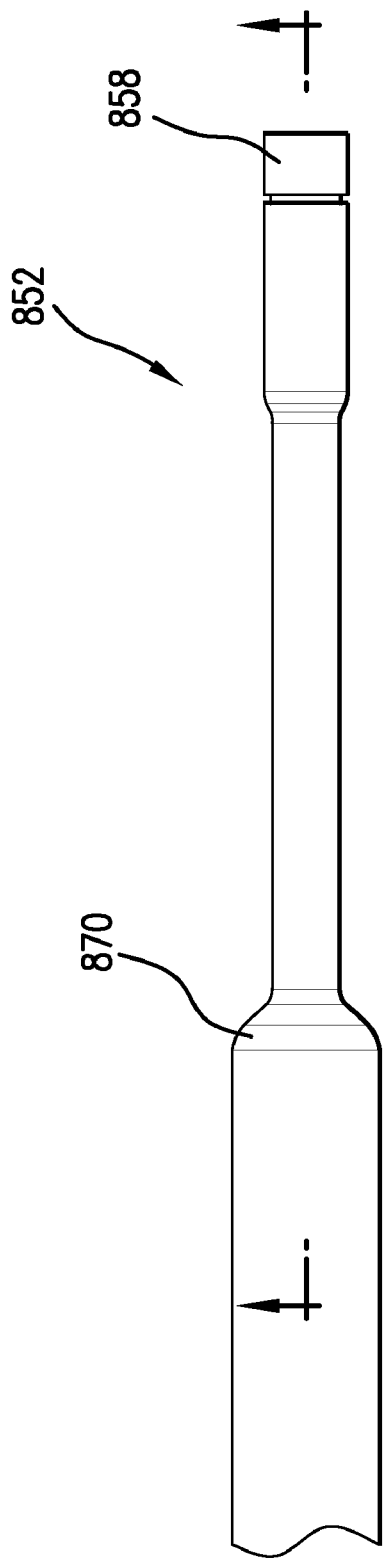
FIG. 27 is an expanded plan view of the distal end of the objects of FIG. 26.
Figure 28:
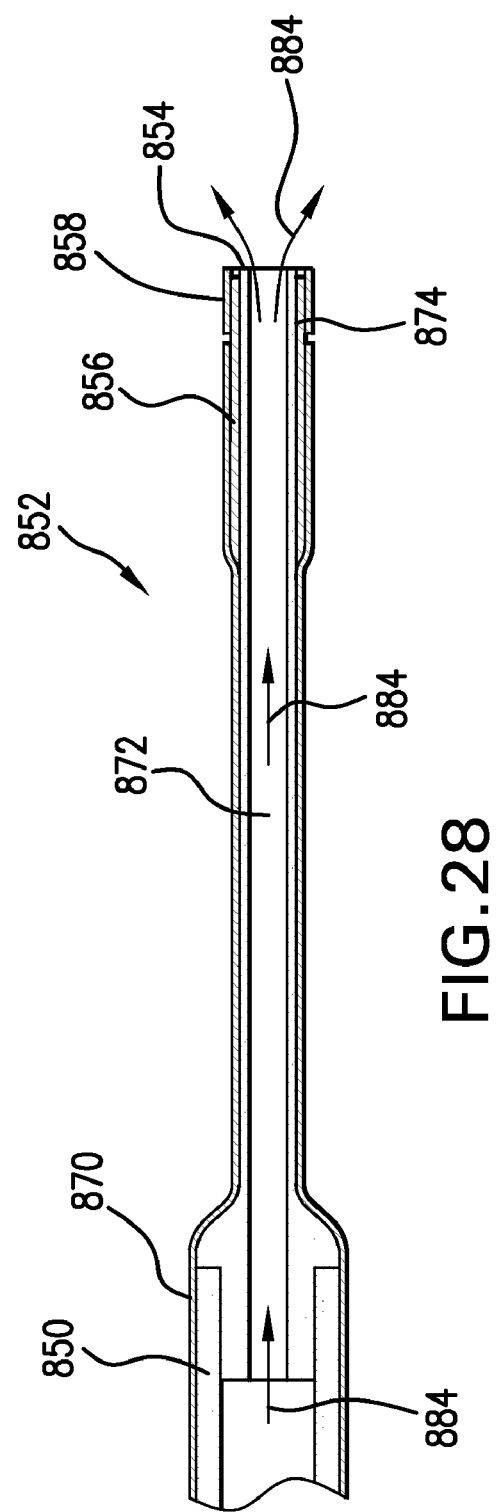
FIG. 28 is a side elevational sectional view of the objects of FIG. 27 as shown in FIG. 27.

The electrosurgical device of the present invention may also be advantageously used for producing holes in tissue. In certain circumstances, such as when making holes with large depth to diameter ratios, it may be desirable to supply conductive fluid to the probe distal end. An embodiment incorporating such a fluid supply means is shown in FIGS. 26 through 28. Electrosurgical probe 840 has a proximal handle portion 842 with buttons 844 and 846 for controlling an electrosurgical power supply to which it is connected by cable 848. Distal portion 850 has a distal tip assembly 852. Tube 880 is connected to a source of conductive liquid which is supplied via a means in handle 842 and a lumen in distal portion 850 to distal tip assembly 852. Referring now to FIGS. 27 and 28, distal tip assembly 852 has an active electrode 854 separated by insulator 856 from floating electrode 858. Dielectric coating 870 covers a proximal portion of insulator 856, a proximal portion of active electrode 854, and the rest of distal portion 850. Lumen 872 supplies conductive liquid 884 to distal end 874 of active electrode 854 and the region surrounding electrode 854, insulator 856 and the distal end of floating electrode 858.

Figure 29:
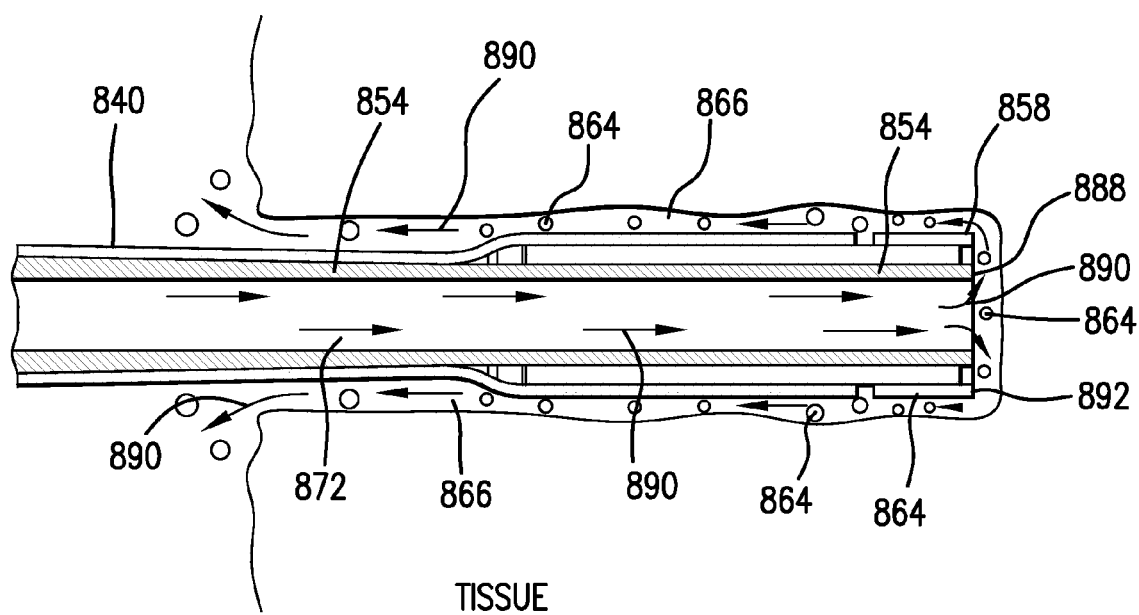
FIG. 29 is a sectional view of the objects of FIG. 27 during use.

Referring now to FIG. 29, during use probe 840 is advanced distally into the tissue, distal surface 888 of active electrode 854 and distal surface 892 of floating electrode 858 having current density sufficient to cause vaporization of tissue. Conductive liquid 890 supplied by lumen 872 fills the region surrounding the probe tip and helps flush bubbles 864 and products of tissue vaporization proximally through gap 866 formed between distal assembly 852 and the tissue. Lower current density heating from the more proximal region 867 of floating electrode 858 desiccates tissue with which it is in contact so as to stop bleeding.

All publications, patent applications, patents and other references mentioned herein are incorporated by reference in their entirety.

While the invention has been described in detail and with reference to specific embodiments thereof, it will be apparent to one skilled in the art that various changes and modifications can be made therein without departing from the spirit and scope of the invention.

What is claimed is:

1. A monopolar electrosurgical probe comprising:
   (a) an elongate shaft having an insulated proximal portion forming a handle and an exposed conductive portion disposed in a distal tip region;
   (b) at least one lumen disposed along the length of said shaft, said lumen having a first port disposed at the proximal end of said shaft and a second port disposed at the distal end of said shaft;
   (c) at least one active electrode located at or near the distal tip of said shaft, said active electrode connected via cabling disposed within said handle to a power supply;
   (d) at least one conductive member disposed at the distal end, wherein said conductive member comprises a floating potential electrode that is not connected to any power supply, said floating potential electrode having a first portion mounted in close proximity to said active electrode and a second portion extended a distance from said active electrode and positioned in a region of low electric potential so as to concentrate the power in the vicinity of the active electrode and increase the energy density in the region surrounding the active electrode; and
   (e) a dielectric member disposed between each active electrode and floating potential electrode.

2. The electrosurgical probe of claim 1, wherein said active electrode has an angled distal surface forming a plurality of parallel ribs separated by grooves.

3. The electrosurgical probe of claim 1, wherein said active electrode and floating electrode form an array of protuberances in which the active and floating electrodes are interspersed, said protuberances enhancing bubble formation at the distal tip and thereby improving probe efficiency.

4. The electrosurgical probe of claim 1, wherein said floating potential electrode comprises an annular ring disposed about said active electrode.

5. The electrosurgical probe of claim 4, wherein said floating potential electrode further includes a plurality of radial slots formed in its distal surface that allow improved irrigation of the region surrounding the probe distal tip, and to increase the current density at the floating electrode distal surface.

6. The electrosurgical probe of claim 1, wherein said at least one lumen is configured to supply conductive irrigant to the distal tip region, such that said first port comprises an inlet port for receiving conductive irrigant and said second port comprises an irrigation outlet port for delivering conductive irrigant to the distal tip region so as to bathe said active and floating potential electrodes in conductive fluid.

7. The electrosurgical probe of claim 1, wherein said at least one lumen is configured to supply a vacuum to the distal tip region, such that said second port comprises an inlet port for aspirating vapor and liquid from the distal tip region and said first port comprises an aspiration port for connecting to a vacuum source.

8. The electrosurgical probe of claim 7, wherein said aspiration port is remote from the distal end of said active electrode so as to minimize both aspiration flow at the active electrode and resulting cooling of said electrode.

9. The electrosurgical probe of claim 1, wherein said probe comprises at least two lumen disposed along the length of said shaft, each lumen having a first port disposed at the proximal end of said shaft and a second port disposed at the distal end of said shaft.

10. The electrosurgical probe of claim 9, wherein one of said two lumen is configured to supply conductive irrigant to the distal tip region and the other of said two lumen is configured to supply a vacuum to the distal tip region.

11. The electrosurgical probe of claim 9, wherein both of said two lumen are configured to supply conductive irrigant to the distal tip region.

12. A method for applying thermal energy to a target tissue comprising the step of:
   (a) introducing the monopolar electrosurgical probe of claim 1 into a surgical site containing said target tissue;
   (b) positioning the distal tip of said probe to be adjacent the target tissue at the surgical site, so that the active electrode and said first portion of the floating potential electrode are in close proximity to the target tissue;
   (c) supplying an irrigant via one of said at least one shaft lumen to the probe distal tip in the region between the active electrode and the target tissue, so as to bathe both active and floating potential electrodes in the irrigant;
   (d) positioning said second portion of said floating potential electrode to be in contact with target tissue, adjacent tissue or conductive irrigant;
   (e) energizing the probe to produce high current density at said surgical site and arcing between said active electrode and said floating potential electrode and/or between said active, said floating potential electrode and said target tissue; and
   (f) effectively heating said target tissue while minimizing heat applied to adjacent tissues.

13. The method of claim 12, further comprising the step of supplying vacuum via another of said shaft lumen so as to remove excess irrigant and ablation products.

14. The method of claim 12, wherein said surgical site comprises a dry environment.

15. The method of claim 14, wherein said target tissue is selected from the group consisting of oral tissue, otolaryngical tissue and dermal tissue.

16. The method of claim 12, wherein said heating step involves ablating and vaporizing the target tissue.

17. The method of claim 16, wherein said probe acts as a drill to produce a hole in said target tissue.

18. The method of claim 12, wherein said heating step involves heating the tissue to a desired temperature for a predetermined duration so as to form a lesion in or on said target tissue.

19. The method of claim 18, wherein said target tissue is selected from the group consisting of cardiac tissue and tumor tissue.

20. The method of claim 12, wherein said irrigant comprises a conductive irrigant.

21. A monopolar electrosurgical probe comprising:
   (a) an elongate shaft having an insulated proximal portion forming a handle and an exposed conductive portion disposed in a distal tip region;
   (b) at least one active electrode located at the distal tip of said shaft and connected via cabling disposed within said handle to a power supply, said active electrode having an angled distal surface forming a plurality of parallel ribs separated by grooves;
   (c) at least one conductive member disposed at the distal end, wherein said conductive member comprises a floating potential electrode comprising an annular ring surrounding said at least one active electrode and not connected to any power source, said annular ring having a plurality of radial slots formed in the distal surface that allow for improved irrigation of the region surrounding the probe distal tip and increase the current density at the floating electrode distal surface, wherein said floating potential electrode further comprises a first portion mounted in close proximity to said active electrode and a second portion extended a distance from said active electrode and positioned in a region of low electric potential so as to concentrate the power in the vicinity of the active electrode and increase the energy density in the region surrounding the active electrode;
   (d) a dielectric member disposed between each active electrode and floating potential electrode; and
   (e) at least one irrigation lumen disposed along the length of said shaft configured to supply an irrigant to the distal tip region, said lumen comprising a first irrigation inlet port disposed at the proximal end of said shaft for receiving the irrigant and a second irrigation outlet port disposed at the distal end of said shaft, between said floating and active electrodes, for delivering the irrigant to the distal tip region so as to bathe said active and floating potential electrodes in the fluid.

22. The electrosurgical probe of claim 21, wherein said irrigant comprises a conductive irrigant.

* * * * *